(12) United States Patent
Sabesan

(10) Patent No.: US 8,049,002 B2
(45) Date of Patent: Nov. 1, 2011

(54) PROCESSES FOR CHEMICAL SYNTHESIS OF LIPOCHITOOLIGOSACCHARIDES

(75) Inventor: Subramaniam Sabesan, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 239 days.

(21) Appl. No.: 12/436,938

(22) Filed: May 7, 2009

(65) Prior Publication Data

US 2009/0292115 A1    Nov. 26, 2009

Related U.S. Application Data

(62) Division of application No. 11/784,253, filed on Apr. 6, 2007, now abandoned.

(60) Provisional application No. 60/790,429, filed on Apr. 7, 2006.

(51) Int. Cl.
| | |
|---|---|
| *C07H 5/04* | (2006.01) |
| *C07H 5/06* | (2006.01) |
| *C08B 37/00* | (2006.01) |
| *C08B 37/08* | (2006.01) |

(52) U.S. Cl. ........ 536/55.1; 536/18.7; 536/20; 536/55.3
(58) Field of Classification Search ................ 536/55.1, 536/18.7, 20, 55.3
See application file for complete search history.

(56) References Cited

U.S. PATENT DOCUMENTS

| 7,485,718 B2 | 2/2009 | Sabesan |
| 2006/0287515 A1 | 12/2006 | Sabesan |

FOREIGN PATENT DOCUMENTS

| DE | 19633502 A1 | 2/1998 |
| WO | 9115496 A1 | 10/1991 |
| WO | 2005063784 A1 | 7/2005 |
| WO | WO 2005/063784 A1 | 7/2005 |
| WO | 2006/102717 A2 | 10/2006 |

OTHER PUBLICATIONS

Orgueira, H.A., Bartolozzi, A., Schell, P., Litjens, R.E.J.N., Palmacci, E.R., Seeberger, P.H. (2003) Modular Synthesis of Heparin Oligosaccharides. Chemistry: A European Journal, vol. 9, No. 1, p. 140-169.*
Banoub, J. (1992) Synthesis of Oligosaccharides of 2-Amino-2-deoxy Sugars. Chemical Reviews, vol. 92, p. 1167-1195.*
Hooper, K.A., Kohn, J. (1995) Diphenolic Monomers Derived from the Natural Amino Acid alpha-L-Tyrosine: An Evaluation of Peptide Coupling Techniques. Journal of Bioactive and Compatible Polymers, vol. 10, p. 327-339.*
Greene, T.W. and Wuts, P.G.M. (1991) Protective Groups in Organic Synthesis, published by John Wiley & Sons, Inc., p. 4, 68-81 and 88-103.*
Stangier, P., Hindsgaul, O. (1996) Solid-Phase Transimidation for the Removal of N-Phthalimido- and N-Tetrachlorophthalimido Protecting Groups on Carbohydrates. SynLett, p. 179-181.*
U.S. Appl. No. 11/154,457, filed Dec. 21, 2006, Subramaniam Sabesan.
Nicolaou et al., Total Synthesis of the NODRM-IV Facots, The *Rhizobium* Nodulation Signal;s, J. Am. Chem. Soc., 1992, vol. 114:8701-8702.
Ikeshita et al., Preliminary Communication NOD BJ-IV (C 18:1 Fuc Gro) Produced by *Bradyrhizobium japonicum* Strain USDA61, Carbohydrate Research 1995, vol. 266:C1-C6.
Wang et al., Chemical Synthesis of NODRM-1: The Nodulation Factor Involved in *Rhizobium meliloti*-Legume Symbiosis, J. Chem. Soc. Perkin Trans., 1994, vol. 1:623-628.
P. Stangier et al., Solid-Phase Transimidation for the Removal of N-Phthalimido-And-Tetrachlorophthalimido Protecting Groups on Carbohydrates, Synlett., 1996, vol. 2:179-181.
Demont-Caulet et al., Nodule Inducing Activity of Synthetic *Sinorhizobium meliloti* Nodulation Factors and Related Lipo-Chitooligosaccharides on Alfalfa. Importance of the Acyl Chain Structure, Plant Physiology, 1999, vol. 120:83-92.
K. C. Nicolaou et al., Journal of the American Chemical Society, 1992, vol. 114, pp. 8701-8702.
M. O. Ramussen et al., Organic and Biomolecular Chemistry, 2004, vol. 2, pp. 1908-1910.
S. Ikeshita et al., Tetrahedron Letters, 1994, vol. 35, No. 19, pp. 3123-3126.
Lai-Xi Wang et al., Tetrahedron Letters, 1993, vol. 34, No. 48, pp. 7763-7766.
P. Groves et al., Organic and Biomolecular Chemistry, 2005, vol. 3, pp. 1381-1386.
T. J. W. Stokkermans et al., Plant Physiology, 1995, vol. 108, pp. 1587-1595.
International Search Report for International Publication No. PCT/US2007/008379 dated Feb. 11, 2008.
Ikeshita et al., Preliminary Communication NOD BJ-IV (C 18:1 Fuc Gro) Produced by *Bradyrhizobium japonicum* Strain USDA61, Carbohydrate Research 1995, vol. 266:C1-C6.
Wang et al., Chemical Synthesis of NODRM-1: The Nodulation Factor Involved in *Rhizobium meliloti*-Legume Symbiosis, J. Chem. Soc. Perkin Trans., 1994, vol. 1:623-628.
P. Stangier et al., Solid-Phase Transimidation for the Removal of N-Phthalimido-And-Tetrachlorophthalimido Protecting Groups on Carbohydrates, Synlett., 1996, vol. 2:179-181.
Demont-Caulet et al., Nodule Inducing Activity of Synthetic *Sinorhizobium meliloti* Nodulation Factors and Related Lipo-Chitooligosaccharides on Alfalfa. Importance of the Acyl Chain Structure, Plant Physiology, 1999, vol. 120:83-92.

* cited by examiner

*Primary Examiner* — Shaojia Anna Jiang
*Assistant Examiner* — Scarlett Goon

(57) ABSTRACT

Processes for the synthesis of lipochitooligosaccharides were developed. A fully acylated oligoglucosamine precursor is prepared and reacted with a glucosamine monomer that has an amine protecting phthaloyl group. With removal of the phthaloyl group, a fatty acid may be added on the terminal glucosamine unit, forming a lipochitooligosaccharide. The processes can be adapted for use on a commercial scale.

3 Claims, No Drawings

PROCESSES FOR CHEMICAL SYNTHESIS OF LIPOCHITOOLIGOSACCHARIDES

FIELD OF THE INVENTION

The present invention is directed to processes for chemical synthesis of lipochitooligosaccharides, and the resulting chemically synthesized lipochitooligosaccharides. The processes disclosed herein allow the stepwise synthesis of low molecular weight N-acylglucosamine oligomers having a fatty acid condensed on the non-reducing end. The processes can be performed on a commercial scale.

BACKGROUND

Lipochitooligosaccharides are naturally made in rhizobial bacteria and function as nodulation factors. The nodulation factors secreted from the bacteria elicit a response in the root cells of legumes that leads to symbiotic nodule formation in the roots. In these nodules nitrogen is fixed, and is provided as a nutrient to the plant. The extent of legume root nodulation is directly linked to plant growth and productivity.

The nodulation factor lipochitooligosaccharides have a backbone of four or five β1,4-linked N-acylated glucosamine residues, a structure also found in chitin (poly-[1-4]-β-N-acetyl-D-glucosamine). This backbone is N-acylated and can carry diverse substitutions at both ends, depending on the rhizobial species in which it is made. In some rhizobia the N-acylation of the terminal unit is with fatty acids of general lipid metabolism such as vaccenic acid (C18:1Δ11Z) and in other rhizobia the N-acylation is with polyunsaturated fatty acids such as C20:3 and C18:2.

The nodulation factor lipochitooligosaccharides made in any one species of bacteria are a mixture of compounds having different substitutions that are not possible to completely separate. Some nodulation factor lipochitooligosaccharides have been chemically synthesized. There are various reported methods for making small samples of lipochitooligosaccharides, for example as described in Nicolaou et al., J. Am. Chem. Soc. 114: 8701-8702 (1992); Ikeshita et al., Carbohydrate Research C1-C6 (1995); and Wang et al., J. Chem. Soc. Perkin Trans. 1: 621-628 (1994).

There remains a need for a process to make the lipochitooligosaccharide class of N-acylglucosamine oligomers in larger quantities and economically. The present invention is related to these and other ends.

SUMMARY OF THE INVENTION

One aspect of the present invention is a process for synthesizing a lipochitooligosaccharide compound having the structure:

Structure A

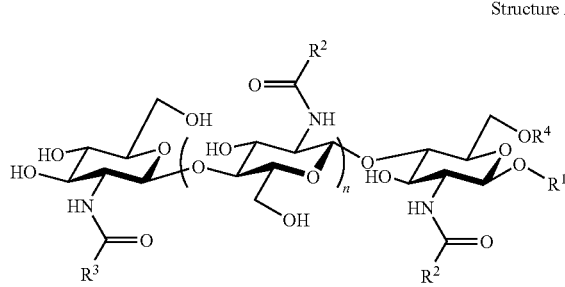

where individual groups $R^1$, and $R^2$ are independently selected from: H, $C_1$ to $C_{20}$ alkyl and aralkyl, aryl, and $C_2$ to $C_{20}$ mono, di or polyalkenyl, mono, di or polyalkynyl groups; $R^3$ is selected from $C_1$ to $C_{20}$ alkyl and aralkyl, aryl, and $C_2$ to $C_{20}$ mono, di or polyalkenyl, mono, di or polyalkynyl, groups; $R^4$ is selected from monosaccharides, sulfates and phosphates; and n is from 0 to about 20;

comprising:
a) combining a compound of structure C

Structure C

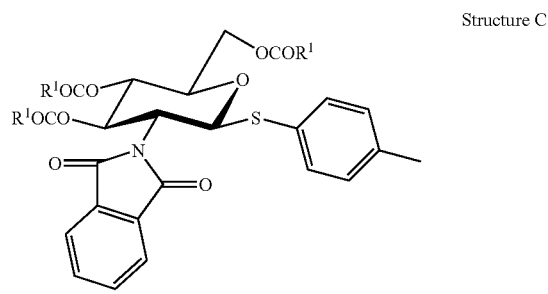

wherein $R^1$ is selected from H, $C_1$ to $C_{20}$ alkyl, aryl, and aralkyl groups, with a compound of structure B Structure B

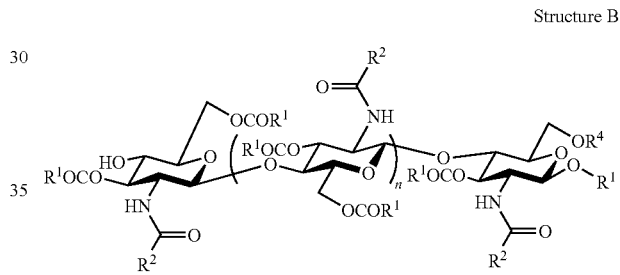

where individual groups $R^1$ and $R^2$ are independently selected from H and $C_1$ to $C_{20}$ alkyl, aryl, and aralkyl groups; $R^4$ is selected from a monosaccharide, a sulfate and a phosphate in a suitably protected form; and n is from 0 to about 19;

in an aprotic solvent and agitating the solution at a temperature between about 0° C. to about –78° C. to form a first mixture;

b) adding to the mixture of a) a first activating agent selected from N-haloimides to form a second mixture;

c) adding a second activating agent selected from perfluoroalkyl sulfonic acids, and optionally adding a reagent selected from methyl perfluoroalkyl sulfonates, to the second mixture to form a third mixture;

d) reacting the third mixture at a temperature between about 0° C. and about –78° C. to form a product comprising ester groups and an N-phthalimido group;

e) isolating the product of d);

f) removing the ester groups and the N-phthalimido group from the isolated product of e) forming a de-esterified and de-N-phthalimido product;

g) isolating the product of f);

h) selectively reacting the amino group of the terminal sugar unit of the isolated product of g) with an acid or acid halide of the formula $R^1COX$:

where X=OH or a halide, for acids and acid halides, respectively, and $R^1$ is selected from H, $C_1$ to $C_{20}$ alkyl, aryl, mono, di or polyalkenyl, mono, di or polyalkynyl groups; to form a lipochitooligosaccharide; and i) isolating the lipochitooligosaccharide.

Another aspect of the present invention is a process for synthesizing a lipochitooligosaccharide compound having the structure:

Structure A

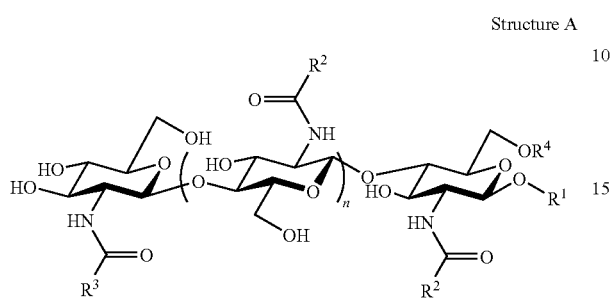

wherein $R^1$ is selected from H, and $C_1$ to $C_{20}$ alkyl and aralkyl, and aryl, groups and $C_2$ to $O_{20}$ mono, di or polyalkenyl, mono, di or polyalkynyl groups; and n is from 0 to about 20;

comprising:

a) providing a compound of structure D

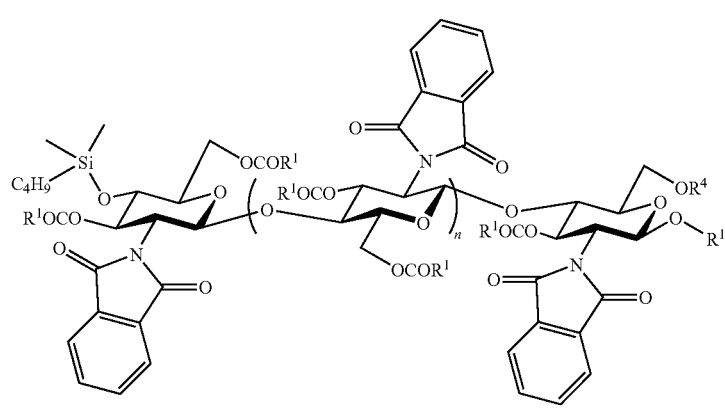

wherein $R^1$ is selected from H, and $C_1$ to $C_{20}$ alkyl, aryl, and aralkyl groups;

b) removing the ester groups and the internal N-phthalimido groups of the compound of structure D;

c) selectively reacting the amino groups on the internal sugar units of the compound of structure D with an acylating reagent to make an N-acyl derivative product;

d) removing the silyl group and the ester and the N-phthalimido group on the terminal sugar unit of the N-acyl derivative product of (c) by reacting the N-acyl derivative product with tetra-N-alkyl ammonium fluoride followed by reacting with amines or diamines under refluxing conditions to produce a de-silylated and de-N-phthalimidated product;

e) acylating the terminal amino group of the de-N-phthalimidated product of (d) with fatty acids activated with carbodiimide and N-hydroxylbenztriazole, or an acid halide of the formula $R^1COX$, in the presence of a base catalyst, where X is a halide, and $R^1$ is selected from H and $C_1$ to $C_{20}$ alkyl, aryl, aralkyl, mono, di or polyalkenyl, mono, di or polyalkynyl groups; to form a lipochitooligosaccharide; and f) isolating the lipochitooligosaccharide.

Another aspect of the present invention is a compound having the structure:

Structure B

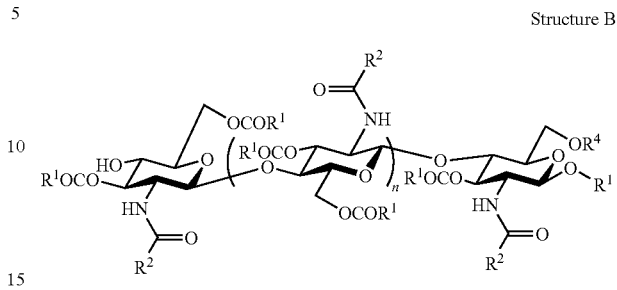

where individual groups $R^1$ and $R^2$ are independently selected from H and $C_1$ to $C_{20}$ alkyl, aryl, groups; $R^4$ is selected from a monosaccharide, a sulfate and a phosphate; and n is from 0 to about 19.

A further aspect of the present invention is a composition comprising a chemically synthesized lipochitooligosaccharide represented by the structure:

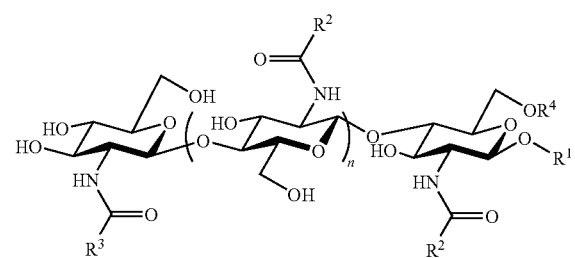

DETAILED DESCRIPTION

The present invention provides processes for synthesizing multigram to kilogram quantities of low molecular weight N-acylglucosamine polymers (oligo N-acylglucosamines) having a fatty acid condensed on the non-reducing end, called lipochitooligosaccharides, that are scalable for commercial use. The processes allow the use of simple purification procedures and do not require cost prohibitive chromatographic separation procedures. The oligo N-acylglucosamine portion of a lipochitooligosaccharide is made by efficient coupling of monomers that are stable to storage. Stepwise addition of a specific type of monomer, described herein below, to a growing polymer chain results in the synthesis of a defined chain length polymer, to which a fatty acid is joined. The glucosamine monomer units are added to each other one at a time, giving the opportunity to select each glucosamine unit in an oligomer and allowing the incorporation of a desired acyl group, including that of a fatty acid, to a glucosamine unit of choice, thus enabling the synthesis of a large array of analogs for biological evaluation.

Also provided are intermediates having the structure:

Structure B

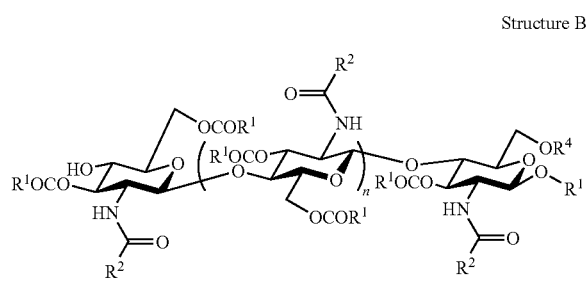

where individual groups $R^1$ and $R^2$ are independently selected from H and $C_1$ to $C_{20}$ alkyl, aryl, and aralkyl groups; $R^4$ is selected from a monosaccharide, a suitably protected sulfate and a phosphate group, each of which is in a suitably protected form; and n is from 0 to about 19. Since each glucosamine unit is added to the chain separately, as described herein below, the individual $R^1$ or $R^2$ group on each glucosamine unit may be different. The intermediates are useful in synthesizing the lipochitooligosaccharides.

When an amount, concentration, or other value or parameter is recited herein as either a range, preferred range or a list of upper preferable values and lower preferable values, the recited amount, concentration, or other value or parameter is intended to include all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Unless otherwise stated, the following terms, as used herein, have the following meanings.

The term "shelf stable," as used herein, means that the compound remains intact with storage at room temperature and when exposed to moisture and air of laboratory storage conditions.

The term "large scale" refers to tens of grams to kilogram quantities of material.

The term "low molecular weight polymer" refers to a chain of monomer units that is greater than one unit and up to about 50 units in length. Oligomers are polymers with two to about 22 units. Therefore an oligo-N-acylglucosamine, for example, is a type of low molecular weight polymer.

The term "linkage position" means the position of the carbon that is a part of the glycosyl bond. In 1,4-, linkages, the linkage position is 1 on one glycoside and 4 on the linked glycoside.

The term "non-linkage position" means the position of a carbon which is not a part of the glycosyl bond. For example, in a 1,4 linkage, the 2, 3 and 6 positions are non-linkage positions.

The term "thioglycoside donor" means the glycosyl molecule that participates at the C-1 position in the glycosyl bond.

The term "glycosyl acceptor" means the glycosyl molecule that has a hydroxyl group at the position that will participate in the glycosyl bond, and that connects through its oxygen to the C-1 glycosyl residue from the donor. In a β1,4-linkage the glycosyl acceptor has a hydroxyl group at the 4 position. The glycosyl acceptor may be a single unit or a multiple unit chain that is a low molecular weight polymer.

The term "suitably protected thioglycoside donor" means a thioglycoside that has protecting groups at the positions that become non-linkage positions following formation of the glycosidic linkage. Protecting groups are used to prevent reaction at those sites.

The term "suitably protected glycoside acceptor" means a glycoside that has protecting groups at the positions that become non-linkage positions following formation of the glycosidic linkage. Protecting groups are used to prevent reaction at those sites.

One embodiment of the present invention includes processes for synthesizing compounds of Structure A:

Structure A

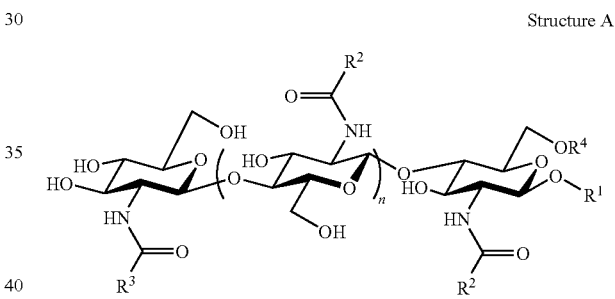

where individual groups $R^1$, and $R^2$ are independently selected from: H, $C_1$ to $C_{20}$ alkyl and aralkyl, aryl, and $C_2$ to $C_{20}$ mono, di or polyalkenyl, mono, di or polyalkynyl groups; $R^3$ is selected from $C_1$ to $C_{20}$ alkyl and aralkyl, aryl, and $C_2$ to $C_{20}$ mono, di or polyalkenyl, mono, di or polyalkynyl, groups; $R^4$ is selected from monosaccharides, sulfates and phosphates; and n is from 0 to about 20. Since each glucosamine unit is added to the chain separately, as described herein below, the individual $R^1$, $R^2$ or $R^3$ group on each glucosamine unit may be different.

In preferred embodiments, the synthesis of compounds disclosed herein, including those of Structure A, are synthesized in sufficiently high yields and with adequate efficiency that allows the processes to be carried out on a commercial scale.

In one process for synthesizing compounds of Structure A, an oligo N-acylglucosamine precursor is synthesized, to which a fatty acid is added forming the $R^3$ group in Structure A. This synthesis is made possible by preparing a fully acylated oligo N-acylglucosamine of Structure B, then adding in β1,4-linkage an N-phthaloyl protected glucosamine monomer through glycosylation with thioglycoside Compound C. The ester and N-phthaloyl groups are removed from the glycosylated product, followed by the addition of a fatty acid to the amino group of the terminal unit to obtain compound A.

The oligo N-acylglucosamine of Structure B to which the terminal phthaloyl-protected glucosamine monomer is added may consist of from 2 to about 21 glucosamine units that are joined by β1,4-linkage.

Structure B

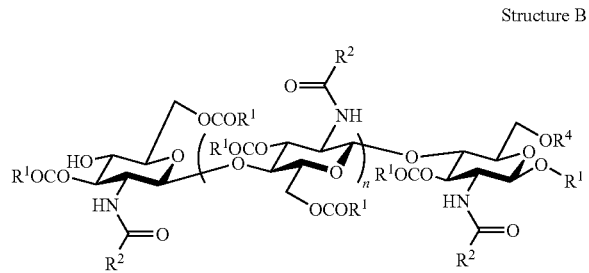

where individual groups $R^1$ and $R^2$ are independently selected from H and $C_1$ to $C_{20}$ alkyl, aryl, and aralkyl groups; $R^4$ is selected from a monosaccharide, a sulfate group and a phosphate group, each of which is in a suitably protected form; and n is from 0 to about 19. Since each glucosamine unit is added to the chain separately, as described herein below, the individual $R^1$ or $R^2$ group on each glucosamine unit may be different.

The N-phthaloyl protected glucosamine monomer that is to be joined to the oligo N-acylglucosamine is shown as Structure C.

Structure C

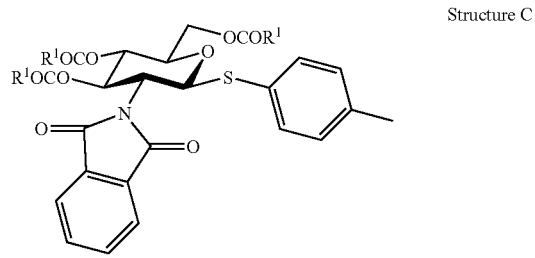

where the $R^1$ groups are independently selected from H, $C_1$ to $C_{20}$ alkyl, aryl, and aralkyl groups.

The oligoglucosamine that is needed for the synthesis of Structure B, is prepared using the process for forming glycosidic linkages between hexoses that is described in U.S. application Ser. No. 11/154,457, which is herein incorporated by reference. The oligoglucosamine is synthesized as follows.

A thioglycoside monomer, represented by Structure (I), is very efficiently coupled to a position 4 glycosyl acceptor represented by Structure (II) by using activating agents generated from N-haloimides and an approximately equimolar amount of a strong protic acid.

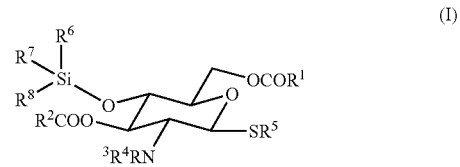

(I)

where $R^1$ and $R^2$ are each independently selected from H and $C_1$ to $C_{20}$ alkyl, aryl, and aralkyl groups;
$R^3$ and $R^4$ are each independently selected from monofunctional acyl, bifunctional acyl, phthaloyl, trichloroacetyl, and tetrachlorophthaloyl groups;

and $R^5$, $R^6$, $R^7$ and $R^8$ are each independently selected from $C_1$ to $C_{20}$ alkyl, aryl, and aralkyl groups.

Preferably $R^1$ and $R^2$ are phenyl groups.

Preferably $R^3$ and $R^4$ are acyl groups derived from a phthaloyl unit.

Preferably $R^5$ is a p-toluoyl group.

Preferably $R^6$ and $R^7$ are methyl groups.

Preferably $R^8$ is a tertiary butyl group.

The position 4 glycosyl acceptor is represented by Structure (II):

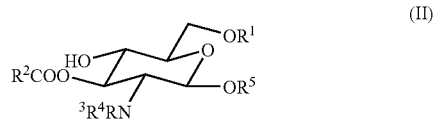

(II)

where $R^1$ is selected from an acyl group and protected glycosyl units;
$R^2$ is selected from H and $C_1$ to $C_{20}$ alkyl, aryl, and aralkyl groups;
$R^3$ and $R^4$ are each independently selected from monofunctional acyl, bifunctional acyl, phthaloyl, trichloroacetyl, and tetrachlorophthaloyl groups; and $R^5$ is selected from $C_1$ to $C_{20}$ alkyl, aryl, and aralkyl groups.

Preferably $R^1$ and $R^2$ are phenyl groups.

Preferably $R^3$ and $R^4$ are acyl groups derived from a phthaloyl unit.

Preferably $R^5$ is a methyl group.

The glycosylation process used in the synthesis of an oligoglucosamine precursor is illustrated as follows. A unit, e.g, molecule, of monomer (II), the glycosyl acceptor, provides an initial unit onto which units of a monomer (I), the thioglycoside donor, are added to extend the polymer chain. Monomers (I) and (II) can be made from D-glucosamine hydrochloride, which is commercially available. To synthesize monomer (I), for synthesis of 1,4-linked glucosamines, the D-glucosamine hydrochloride is derivatized with a phthaloyl group using phthalic anhydride to protect the amine (product 2 in Example 1). The hydroxyl groups are then protected by acetylation (product 3 in Example 2), and the product is purified by crystallization. Next, a benzenethiol group is added to the 1 position (product 4 in Example 2) and the product is purified by washing with protic solvents. The resulting product is deacetylated (product 5 in Example 2), benzoyl protecting groups are added at the 3 and 6 hydroxyl positions (product 6 in Example 2) and the product is purified by crystallization. Finally a silicon protecting group, referred to as a t-butyldimethylsilyl (tBDMS) group, is added as a temporary protecting group at the 4-hydroxyl group of product 6, creating the compound shown as monomer (I) in Reaction 1 below (S-(p-toluoyl)4-O-(dimethyl-t-butyl silyl)-2-deoxy-3,6-di-O-benzoyl-2-phthalimido-1-thio-β-D-glucopyraoside). This compound represents one example of a monomer (I), which is a suitably protected thioglycoside donor. Each of the individual reactions used in the preparation of monomer (I) is known to one skilled in the art. The combination of reactions and purifications is amenable to large scale preparation of monomer (I), which is used in the process of the instant invention. The resulting monomer (I) provides a building block for the synthesis of oligoglucosamines.

One skilled in the art will know that other protecting groups can be used in the preparation of intermediates to glucosamine-monomer (I). For example, the amine can be protected with monofunctional acyl, bifunctional acyl, trichloroacetyl or tetrachlorophthaloyl groups and the hydroxyl groups can be protected with $C_1$ to $C_{20}$ alkyl, aryl, or aralkyl groups as a part of an ester group. Similarly, the silyl group can be any tri-substituted silicon, substituted with, for example, $C_1$ to $C_{20}$ alkyl, aryl, and aralkyl groups.

To synthesize monomer (II), for synthesis of 1,4-linked glucosamine, a similar sequence of reactions as used for monomer (I) is used. The phthaloyl derivative of D-glucosamine hydrochloride (product 3 in Example 2) is acetylated and methylated at the 1 position hydroxyl (product 7 in example 3), then deacetylated at the other hydroxyls (product 8 in example 3). Benzoyl groups are added to product 8 at the 3 and 6 positions creating monomer (II). Alternatively, a hydroxyl-protected monosaccharide may be added to the 6 position. Each of these individual steps is carried out using reaction conditions well known to one skilled in the art. The resulting monomer (II) provides the initial unit onto which molecules prepared as for monomer (I) are added for the synthesis of a low molecular weight glucosamine. The compound shown in Reaction 1 below (methyl 2-deoxy-3,6-di-O-benzoyl-2-phthalimido-β-D-glucopyraoside) represents one example of a monomer (II) type compound, which is a suitably protected glycosyl acceptor containing a hydroxyl group at the 4-position.

One skilled in the art will know that other protecting groups can be used in the preparation of intermediates to monomer (II). For example, the amine may be protected with monofunctional acyl, bifunctional acyl, trichloroacetyl or tetrachlorophthaloyl groups and the hydroxyl groups may be protected with $C_1$ to $C_{20}$ alkyl, aryl, or aralkyl groups as a part of an ester group.

Through iterative glycosylation and silicon protecting group removal from the product polysaccharide, glycosyl units can be added to the desired length. Coupling of monomers (I) and (II), as well as coupling of an oligoglucosamine chain+monomer (I), is carried out using thioglycoside activating agents under saturating substrate concentration in the reaction. The thioglycoside activating agents are generated from N-haloimides and strong protic acids. For example, N-halosuccinimides such as N-iodosuccinimide and N-bromosuccinimide can be used as activating agents in combination with strong protic acids such as triflic acid (trifluoromethanesulfonic acid) and other perfluoroalkylsulfonic acids. Though triflic acid alone is sufficient to activate the thioglycoside, the combined use of triflic acid and methyltriflate (methyltrifluoromethanesulfonate) facilitates the removal of by-products that may be detrimental to the glycosylation reaction. Thus, while methyltriflate is not sufficient to activate the monomer (I), the combination of triflic acid/methyltriflate provides optimal efficiency for reaction and purification conditions.

Use of N-halosuccinimide at 1 to 1.8 molar equivalent to monomer (I) and approximately a molar equivalent (to monomer (II)) amount of any perfluoroalkyl sulfonic acid, of which triflic acid is an example, together with a molar equivalent (to monomer (II)) of methyltriflate provides efficient glycosylation. Use of triflic acid in amounts of about 0.25 to about 1.0 molar equivalent amount can be employed for effective glycosylation. The coupling efficiency is directly related to the ease of purification of the desired product from starting material. Thus of particular use is approximately a molar equivalent amount each of triflic acid and methyltriflate, for forming a readily purifiable product. Such high concentrations of triflic acid do not cleave the sugar molecule, especially when the reaction is carried out at low temperatures.

Using the above described activating agents, the coupling reaction can be driven to quantitation, forming the glycosidic linkage, as shown in Reaction 1. Shown is an example reaction of glucosamine-monomer (I) and glucosamine-monomer (II) forming a dimer low molecular weight polyglucosamine. The coupling of monomer (I) to the glycosyl acceptor (in this case monomer (II)) is step A.

Reaction 1

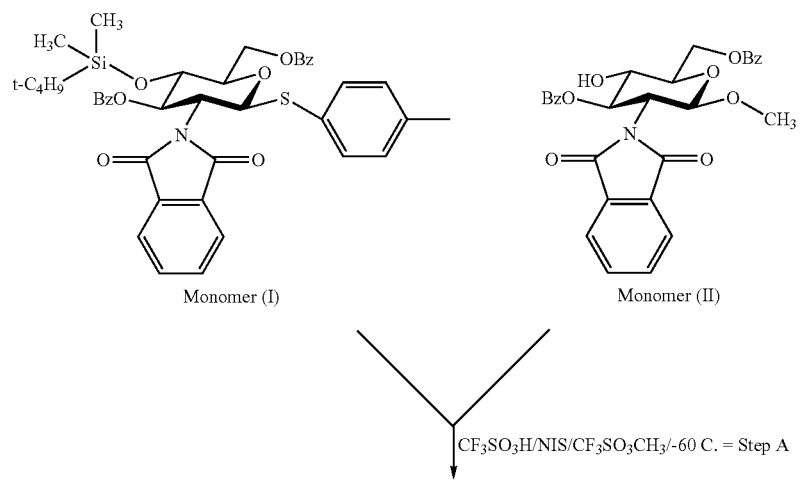

-continued

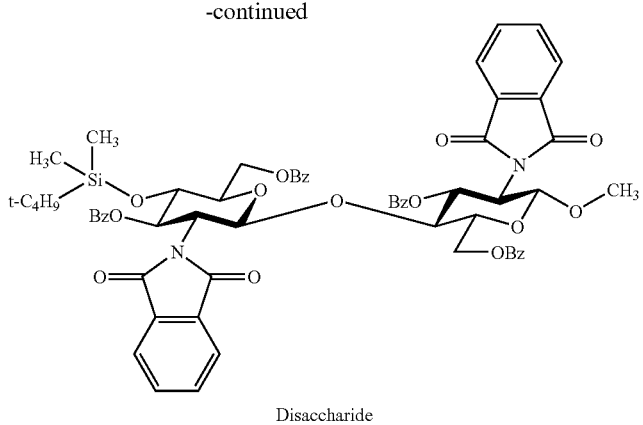

Disaccharide

NIS = N-Iodosuccinimide
Bz = Benzoyl (C$_6$H$_5$CO)

In addition, using a minimum amount of reaction solvent keeps the reactants at saturation levels and at high effective concentration, and results in more efficient glycosylation. The activating agents are added to the glycosides and the coupling reaction is carried out at a low temperature. Temperatures from about 0° C. to about −78° C. are suitable for the reaction. It is preferred that the temperature for the reaction be between about −20° C. and about −70° C. More preferred is that the temperature be between about −50° C. and about −60° C. The reaction time is from about 15 minutes to about 8 hours. The reaction is desirably allowed to run for a time sufficient for all potential glycosidic linkages to be formed. Preferred is a reaction time between about 4 and about 6 hours.

A general description of a process for coupling of monomer (I), a suitably protected thioglycoside donor, and monomer (II), a position 4 glycosyl acceptor, is as follows. Monomer (II) (about 1.0 eq.) and monomer (I) (at least 1 and up to about 3 eq., with about 1-2 eq. being preferred) are dissolved in a minimum of an aprotic solvent, such as methylenechloride, diethylether, acetonitrile, and benzotrifluoride. The most preferred solvent is methylenechloride. The solution is cooled to about −55° C. to −60° C. under nitrogen atmosphere with agitation. Agitation may be by any method which thoroughly mixes the components of the solution, such as shaking or stirring. Typically, vigorous stirring is used. Powdered N-Iodosuccinimide (NIS) is added to the cold solution. After about 15 min, a solution of a perfluoroalkyl sulfonic acid, such as triflic acid (about 1.0 eq.) and methyltrifluoromethanesulfonate (about 1.0 eq.), dissolved in minimum of aprotic solvent, e.g., methylenechloride, is added in drops, while maintaining the reaction temperature under about −60° C. After the addition, the reaction mixture is maintained at the same temperature with stirring, for about 6 hours and then poured directly over a 1:1 mixture of saturated sodium thiosulfate and saturated sodium bicarbonate solution. Additional solvent such as methylenechloride is employed to dilute the reaction mixture and provide washing of the reaction flask. The solution is thoroughly mixed and the organic layer separated. The organic layer is then washed sequentially with 1% to 6% bleach solution, preferably 0.6% to 3% bleach solution, then water, and finally with saturated sodium bicarbonate solution. The product is recovered by concentration of the solution at reduced pressure. The impurities are removed by dissolving the material in diethylether or ethylacetate, followed by precipitation with n-hexane. It is to be understood that variations known to one skilled in the art can be introduced into the process, without departing from the scope of the invention.

The efficiency of the described coupling reaction reduces the level of undesired by-products and starting materials in the reaction mixture following coupling, thereby facilitating the removal of the existing minor impurities through selective solvent extraction methods. There is no need for the commonly used and expensive purification methods of silica gel chromatography, although these methods may be used. Selective washing with organic solvents provides a simplified purification method that is useful for large-scale production. Solvents useful for the washing during purification include diethylether and hexane-ethylacetate mixture. Any combination of solvents in which the product is insoluble, but the impurities and the by-products are soluble, may be used. This selective extraction of impurities derived from excess monomer (I), using solvents in which the desired product is insoluble, is a highly preferred method for isolation of the product.

Following coupling and optional purification, chain extension is carried out. Prior to extension of the disaccharide product, the silicon blocking group is removed from the polyglucosamine linkage position as shown in Reaction 2 below, step B. The silicon group can be removed, for example, by dissolving in minimum anhydrous tetrahydrofuran (THF), then reacting with acetic acid (2-3 eq.) and n-tetrabutylammonium fluoride solution in THF (1 M, 2-3 eq.). The reaction progress may be monitored either by TLC or NMR of the reaction mixture. Additional methods for removing silicon protecting groups are well known to one skilled in the art.

Upon completion, the reaction mixture is concentrated to dryness, the residue dissolved in solvent such as methylenechloride and washed with water, 1M aqueous HCl solution, 0.6%-3% bleach solution (to remove the dark brown color), and aqueous saturated sodium bicarbonate solution. The remaining organic layer is dried over anhydrous magnesium sulfate and concentrated to dryness. Purification of the product is typically accomplished by precipitation with, for example, diethylether or an n-hexane-ethyl acetate mixture, which ensures the removal of residual monomer from the previous step as well as the silicon impurity. Any combination of solvents in which the product is insoluble, but the impurities and the by-products are soluble may be used for precipitation.

Additional monomer (I), a suitably protected thioglycoside donor, is then added through a glycosyl bond to the unblocked disaccharide using activating agents as described above. The disaccharide is used in place of monomer (II), as shown in Reaction 2, according to the general coupling procedure described above. Shown is an example reaction of a glucosamine dimer with removal of the silicon blocking group in step B and addition of a glucosamine-monomer (I) forming a trimer low molecular weight polyglucosamine. The coupling of monomer (I) to the glycosyl acceptor (in the example reaction, the glucosamine dimer) is step A.

oligoglucosamine used in synthesis of a lipochitooligosaccharide. The polyglucosamine chain length may be between 2 and about 21 units. Chain lengths of between about three and about seven units are particularly suitable for use in the present process.

The benzoyl and phthalimido protecting groups on the precursor oligoglucosamine are then converted to their acetates. The protecting groups are removed by methods well known by one skilled in the art. For a polymer containing 2-5 residues, this is carried out in a two step procedure. First, de-O-benzoylation can be accomplished by Zemplens'

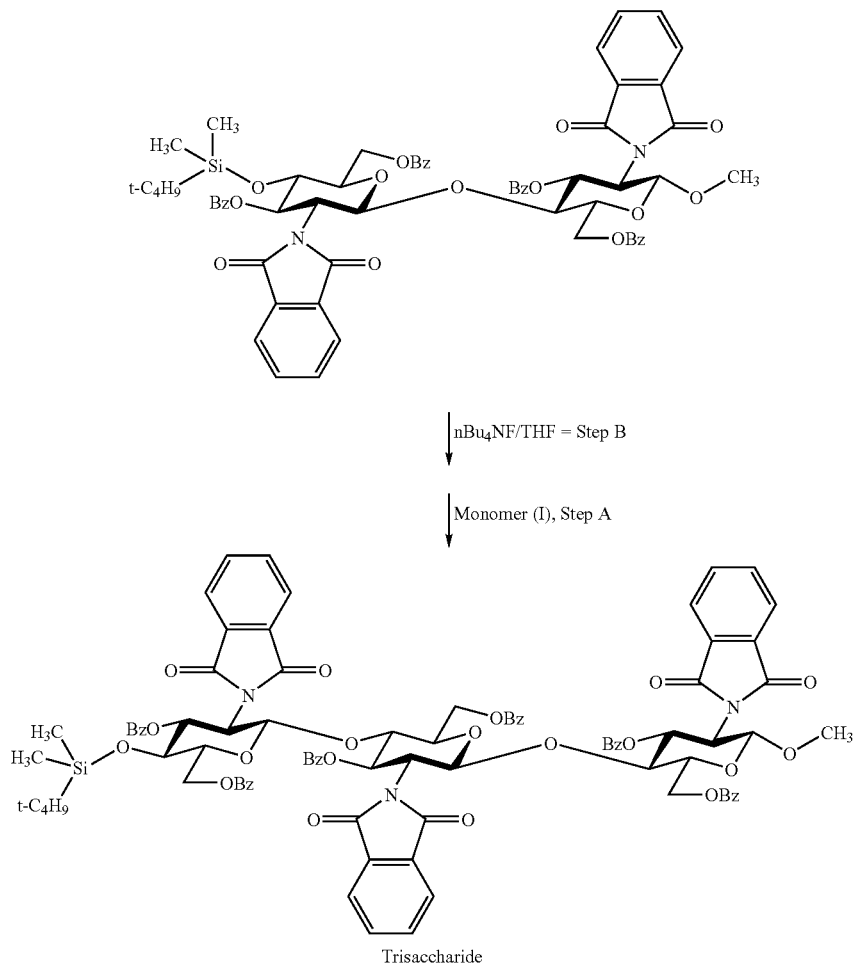

Reaction 2 nBu$_4$NF/THF = Step B

Monomer (I), Step A

Trisaccharide

Purification by organic solvent washing is also as described above. Further rounds of chain extension are accomplished by silicon blocking group removal and addition of monomer (I). The process is repeated in a stepwise manner such that the thioglycoside and the polyglucosamine form a beta linked polyglucosamine that has a length of x+1, wherein x is the length of the starting polyglucosamine and 1 is one monomer unit. Since the reaction at each step is nearly quantitative, the completion of each step results in a product that contains more than about 80% of molecules having a single chain length. Thus the product is enriched in a single anomer of beta linkage oligoglucosamine molecules.

The steps are repeated until a polyglucosamine chain is made that is of unit length appropriate to form the precursor method, which is well known to those skilled in the art, using sodium methoxide in methanol. The phthaloyl group can be removed by using an ethylenediamine-derivatized Merrifield resin (P. Stangier, O. Hindsgaul, Synlett. 1996, 2: 179-181), as well known to one skilled in the art. Alternatively, removal of the benzoyl and the phthalimido groups can be accomplished in a single step by treating the protected product at refluxing temperature with hydrazine or hydrazine in n-butanol, followed by selective extraction of the product polyhexosamine with water. The single step method is preferred for polymers of length greater than 4, due to their incomplete de-benzoylation under Zemplens' condition and their lack of solubility in methanol and n-butanol. The silyl protecting group remains on the terminal 4-hydroxyl group at the chain extension end.

The hydroxyl and the amino groups of the resulting compound are then acylated using procedures well known to those skilled in the art. For simple acyl groups such as an acetyl group, acylation can be carried out by addition of pyridine and acetic anhydride, with addition of a small amount of 4-N,N-dimethylamino pyridine, as is well known to one skilled in the art. Anhydrides of simple acyl groups, such as acetyl or propionyl groups, are commercially available and are readily used. For other types of acyl groups where anhydrides are not available, the corresponding acid chlorides are used. It is desired that the acyl groups at the amino groups stay permanently, as seen in the lipochitooligosaccharide molecule, whereas the acyl groups at the hydroxyl function are removed. Also there may be differential introduction of acyl groups at the amino and hydroxyl functions if desired, by acylating the highly reactive amino groups first, followed by acylation of the hydroxyl groups by methods well known to one skilled in the art.

The silicon blocking group is then removed from the resulting compound as described previously in the polyglucosamine chain extension reaction. The resulting N- and O-acyl oligoglucosamine compound is shown as Structure B above. The compound of Structure B is then reacted with the compound of Structure C (which has a protecting phthaloyl group; structure shown above). The compound of Structure C is an intermediate in the synthesis of Monomer (I), and its preparation is as for Product 4 in Example 2, which is the same compound as shown in Structure C. The reaction of a compound of Structure B and a compound of Structure C is carried out as described above for coupling of Monomers (I) and (II), as well as coupling of an oligoglucosamine chain+Monomer (I). The resulting coupled Structures B+C product is isolated as described above for the coupled Monomers (I)+(II) product.

The protecting N-phthalimido group and the ester groups of the coupled Structures B+C product are removed in a two-step reaction, using conditions well known by one skilled in the art. The ester groups are first removed by transesterification with metal alkoxides in alcohol, specifically by treating the ester with sodium methoxide in methanol. The N-phthaloyl group is then removed by reacting with amines or diamines under refluxing conditions, specifically by treating the de-esterified product with hydrazine in alcoholic solvents such as methanol and ethanol, or by treating the de-esterified product with ethylenediamine derivatized Merrified resin. The de-esterified product with phthalimido group removed is isolated by extracting with water, and removing the impurities by washing the aqueous layer with solvents capable of extracting the impurities, such as methylene chloride. The resulting compound has a free amino group on the terminal sugar unit, while all other nitrogens are acylated.

Another process for making a compound having a free amino group on the terminal sugar unit, while all other nitrogens are acylated, may be carried out starting with a compound of structure D:

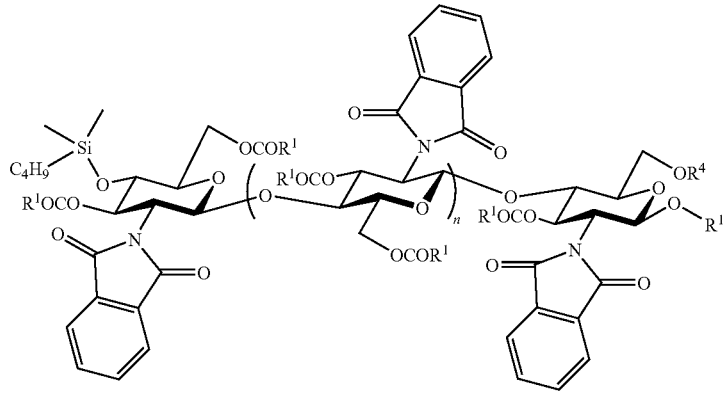

Structure D wherein $R^1$ is selected from H, and $C_1$ to $C_{20}$ alkyl and aralkyl, and aryl, groups and $C_2$ to $O_{20}$ mono, di or polyalkenyl, mono, di or polyalkynyl groups;

The compound represented by structure D can be synthesized according to the process described in the Examples herein for synthesizing Product 13. The ester groups are removed under transesterification conditions using metal alkoxides in alcohols under refluxing conditions. The internal N-phthalimido groups are removed by reacting with ethylenediamine resins. Acylation of internal amino groups are carried out by methods well known to one skilled in the art, followed by removing the silyl group and the ester and the N-phthalimido group on the terminal sugar unit by reacting with tetra-N-alkyl ammonium fluoride, followed by reacting with amines or diamines under refluxing conditions to produce a de-silylated and de-N-phthalimidated product containing a free amino group on the terminal sugar unit.

The free amino group is selectively reacted with an acid or acid halide of the formula $R^1COX$:

where X=OH or a halide, for acids and acid halides, respectively, and $R^1$ is selected from H, $C_1$ to $C_{20}$ alkyl, aryl, aralkyl, alkenyl, dienyl, and trienyl groups.

Typically the acid halide is a chloride reagent, but bromides and iodides may also be used.

The reaction of the free amino group on the terminal sugar of the coupled Structures B+C product, with the protecting N-phthalimido group and the ester groups removed, and $R^1COX$ may be performed by methods well known by one skilled in the art (some of which are described in WO2005063784A1). For example, reactants may be dissolved in a DMF-water mixture, or water and methanol or ethanol mixture. When an acid halide is employed in the reaction, base catalysts such as sodium carbonate, potassium carbonate, bicarbonate, triethylamine, or hydroxides of alkali or alkaline earth metals are used. When acids are employed in the amidation reaction, it is carried out in the presence of a carbodiimide such as ethyl-(N,N-dimethylaminopropyl)-carbodiimide hydrochloride, and N-hydroxybenzotriazole may be added to promote the reaction. The product may be isolated by methods known to those skilled in the art such as by filtering through an acidic resin column, followed by drying. The reaction results in an N-acylglucosamine compound having a fatty acid condensate linked at the amino group of the terminal residue, having a Structure A (shown above), which is called a lipochitooligosaccharide. Compounds made in the present process may have one or more fatty acid groups on internal residues as well. During the synthesis of compounds of Structure B, the glucosamine monomer units are added to each other one at a time, giving the opportunity to select each glucosamine unit in an oligomer and allowing the incorporation of a desired acyl group, including that of a fatty acid, to a glucosamine unit of choice. Thus a fatty acid may be incorporated with a glucosamine unit at an internal position, in addition to adding a fatty acid to the terminal glucosamine unit.

Lipochitooligosaccharides include natural nod factors that are signaling factors involved in nodulation of legume roots by nitrogen fixing bacteria. Through increasing nodulation, thereby increasing the nitrogen supply to the plant, lipochitooligosaccharide nod factors enhance plant growth and yield. Lipochitooligosaccharides may be used to treat the roots, leaves, or seeds of plants. The compounds may be applied in the soil, to plant foliage, or as a seed coating. Both legume and non-legume plants may benefit from these treatments.

Individual lipochitooligosaccharides prepared using processes disclosed herein may be readily tested for effects on legume root nodulation by one skilled in the art, for example as described in Demont-Caulet et al. (Plant Physiology 120: 83-92 (1999)). Also the effectiveness of individual lipochitooligosaccharides, prepared using processes disclosed herein, in promoting plant growth enhancement and yield improvement of legume and non-legume plants may be readily tested, as is well known to one skilled in the art. Thus compounds of Structure A which do not correspond to known natural nodulation factors, but which have nodulation stimulating activity, plant growth enhancing activity, or yield enhancing activity may be prepared using processes disclosed herein and readily identified by testing for these applications.

EXAMPLES

General Methods and Materials

Unless specified, all the reagents were purchased from Aldrich Chemical Co (St. Louis, Mo.). Thin layer chromatography was performed on pre-coated plates of Silica Gel 60 $F_{254}$ (EM Science) and the spots were visualized with a spray containing 5% sulfuric acid in ethanol, followed by heating. Column chromatography was done on silica gel 60 (230-400 mesh, EM Science). $^1$H NMR spectra were recorded at 500 MHz. The hydrogen chemical shifts in organic solvents are expressed relative to deuterated methylenechloride, with a reference chemical shift of 5.36 ppm. For solutions of compounds in deuterium oxide or deuterated methanol, the hydrogen chemical shift values are expressed relative to the HOD signal (4.75 ppm at 296° K).

Example 1

Synthesis of 2-deoxy-1,3,4,6-tetra-O-acetyl-2-phthalimido-D-glucopyranose

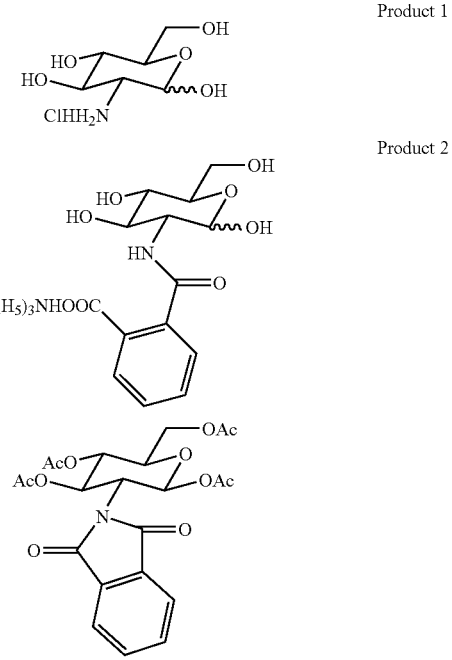

D-Glucosamine hydrochloride (compound 1, 1.0 Kg) was suspended in methanol (5.0 L) and vigorously stirred. NaOH (184.8 g) was dissolved in minimum deionized water and added to the D-Glucosamine/Methanol suspension. The suspension was stirred for 15 min and the insoluble material (sodium chloride) was filtered off by vacuum filtration. The theoretical amount of NaCl formed should be about 270 g.

To the filtrate, phthalic anhydride (342 g) was added and the solution was stirred until most of the solid dissolved (about 30 min). This was then followed by the addition of triethylamine (468 g) and stirred for 10 to 15 min. To the resulting clear solution, another portion of phthalic anhydride (342 g) was added and the mixture was allowed to stir overnight at room temperature. Product usually began to precipitate out after two hours.

The precipitated product was filtered and the residue was washed with minimum ice cold methanol so as to remove the yellow color from the product. The residue was then washed three times with acetonitrile, with enough solvent added to the filter to completely immerse the solid, and dried at room temperature under high vacuum. The weight of the white solid, product 2, was 954 g. $^1$H-NMR ($D_2O$): 7.74-7.56 (phthalimido hydrogens), 5.42 (H-1α), 4.94 (H-1β), 4.17 and 4.01 (H-6), 3.27 ($CH_2$ of N-ethyl group), 1.35 ($CH_3$ of N-ethyl group).

The product 2 from above (1.01 Kg, made from two batches) was placed in a 10 liter 3 neck round bottom flask set up with an overhead electric stirrer, an $N_2$ inlet and an addition funnel. Acetic anhydride (3 L) and N,N-dimethylaminopyridine (1.0 g) were added to the flask and stirred vigorously. Pyridine (2.8 L) was added slowly and the reaction mixture was stirred for 2 days at room temperature. The reaction mixture was quenched with ice-water (4 L) and the product was extracted with methylenechloride. The organic layer was repeatedly washed with aqueous hydrochloric acid solution, and then with saturated sodium bicarbonate solution. The organic layer was dried over anhydrous magnesium sulfate, filtered, and concentrated to dryness. The product was recrystallized from hot ethanol. Weight of the recrystallized product 3 was 701 g. $^1$H-NMR (CD$_2$Cl$_2$) δ: 7.91-7.80 (phthalimido hydrogens), 6.62 (H-1), 5.59 (H-3), 5.21 (H-4), 4.47 (H-2), 4.36 and 4.16 (H-6), 4.06 (H-5), 2, 12, 2.06, 2.02, 1.88 (acetyl methyl groups). Thus the above NMR chemical shift data verified the structure of product 3,2-deoxy-1,3,4,6-tetra-O-acetyl-2-phthalimido-D-glucopyranose, which is shown below in Example 2.

Example 2

Synthesis of Monomer (I)

Preparation of Intermediate Product 4:

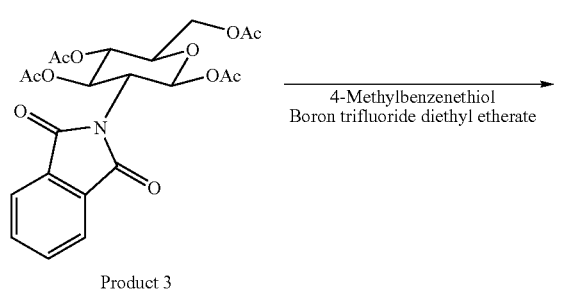

Product 3

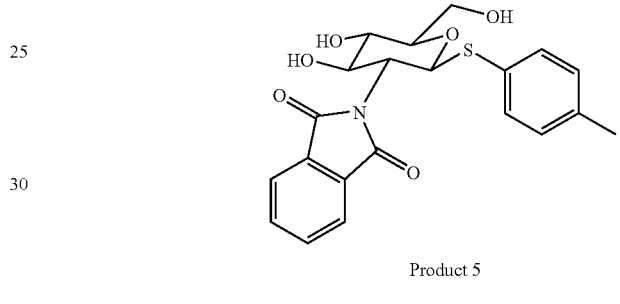

Product 4

Product 3 (464 g) was dissolved in toluene and the solvent was evaporated. This was repeated and the remaining solid was placed on a high vacuum line overnight.

The dried solid was dissolved in minimum methylenechloride (ca. 600 ml), and stirred well. To this, 4-methylbenzenethiol (181 g, 1.45 mol, 1.5 eq.) was added followed by the dropwise addition of boron trifluoride diethyl etherate (BF3-etherate; 165 g, 1.16 mol, 1.2 equivalent, over 180 min). The reaction mixture was stirred overnight. White crystals formed in the morning when stirring was stopped. The crystals were filtered, giving product 4A. The filtrate was diluted with methylenechloride, washed sequentially with saturated NaHCO3 solution, water, then bicarbonate solution, and dried giving product 4B. Both 4A and 4B products were extensively washed with anhydrous methanol and dried under vacuum. Since the NMR spectrums of 4A and 4B products were identical, these two were combined (Product 4, 426.3 g).

$^1$H-NMR (CD$_2$Cl$_2$) δ: 7.96-7.80 (phthalimido hydrogens), 7.36 & 7.13 (S-aromatic hydrogens), 5.78 (H-3), 5.69 (H-1), 5.13 (H-4), 4.33 (H-2), 4.30 & 4.12 (H-6), 3.93 (H-5), 2.36 (S-Ph-Me group), 2.13, 2.04, 1.85 (methyls of acetyl groups). Thus the NMR spectrum verified the structure of product 4, as shown above.

Preparation of Intermediate Product 5

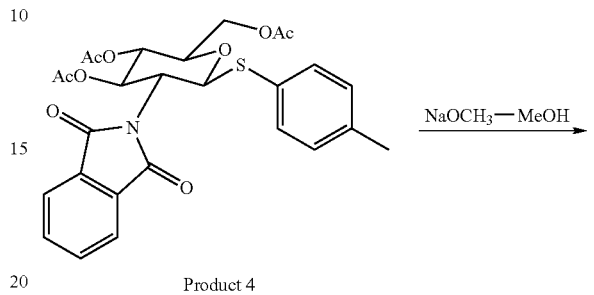

Product 4

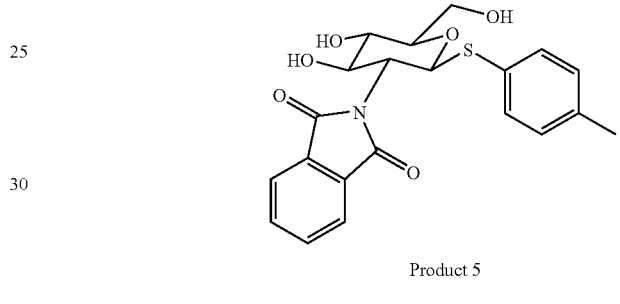

Product 5

Product 4 (350 g) was suspended in nearly 4 L of dry methanol. To this, 35 ml of 0.5 M sodium methoxide solution was added and the solution immediately turned basic. The suspension was left stirring at room temperature overnight. The solid deposited was filtered and washed with dichloromethane, giving pure Product 5 (232 g). The filtrate was neutralized with sulfonic acid resin and concentrated to dryness. The dry solid was washed with methylenechloride and dried, giving impure compound 5 (43.8 g). $^1$H-NMR (CD$_3$OD) of pure 5 δ: 7.87-7.76 (phthalimido hydrogens), 7.22 & 6.99 (S-aromatic hydrogens), 5.46 (H-1), 4.18 (H-2), 4.03 (H-3), 3.89 & 3.70 (H-6), 3.39 (H-5), 3.37 (H-4), 2.22 (S-Ph-Me group). Thus the NMR spectrum verified the structure of product 5, as shown above.

Preparation of Intermediate Product 6

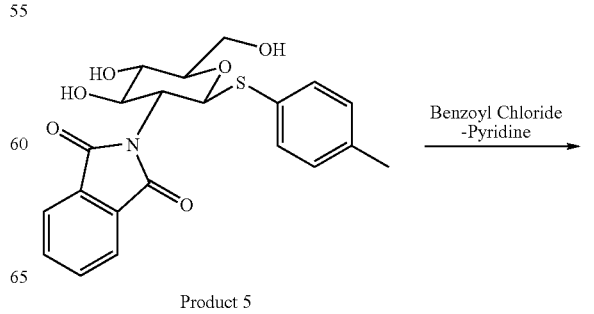

Product 5

-continued

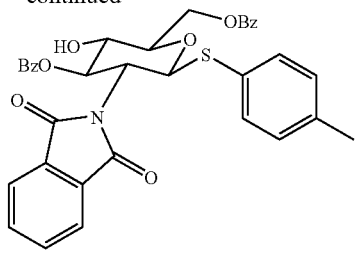

Product 6

Bz = C₆H₅CO

Product 5 (295 g; 638; mmol) was suspended in dry toluene (1 L) and evaporated under vacuum. This procedure was repeated once more to ensure the removal of methanol contaminant that is detrimental to the reaction. 265 grams total was recovered. The residue after toluene evaporation was suspended in methylenechloride (3 L) in a 3-neck flask fitted with an overhead stirrer and the suspension was stirred under dry nitrogen atmosphere. The flask was cooled in an ice bath and the following reagents were added: Pyridine=126 g, N,N-Dimethylaminopyridine=500 mg; and Benzoyl Chloride: 171 g (added by means of an addition funnel slowly in drops over 60 min). The reaction mixture was milky white, but began to clear when all benzoyl chloride was added. The reaction was allowed to stir for 18 h at room temperature. The reaction was diluted with methylenechloride and was washed with water (2×), 1 M aqueous HCl (2×), then saturated NaHCO₃ and dried with MgSO₄.

The crude product was recrystallized in 8 liters of hot EtOH, crystals were filtered, and washed in EtOH giving Crop 6A (225 g). The filtrate was concentrated to dryness giving Crop 6B (131 g). A second recrystallization of Crop 6A was done to give pure product 6 (172 g). The residue (40 g) from the filtrate of the second recrystallization had product 6 of purity greater than 95%, as determined by NMR. Crop 6B was not further processed as NMR analysis showed that it had a significant amount of undesired products and was therefore recycled back to compound 5.

¹H-NMR (CD₂Cl₂) δ: 8.14, 7.88, 7.69, 7.57, 7.41 (benzoate hydrogens), 7.80-7.72 (phthalimido hydrogens), 7.34 & 7.00 (S-aromatic hydrogens), 5.93 (H-3), 5.79 (H-1), 4.77 & 3.99 (H-6), 4.47 (H-2), 4.03-3.99 (H-5), 3.91 (H-4), 3.25 (OH), 2.31 (S-Ph-Me group). Thus the NMR spectrum verified the structure of product 6, as shown above.

Preparation of Monomer (I)

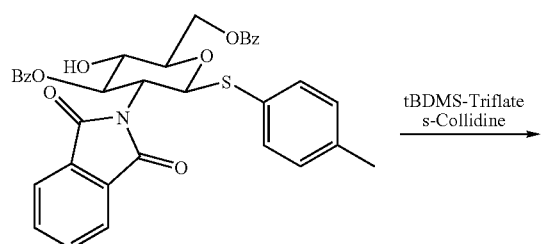

Product 6 tBDMS-Triflate s-Collidine →

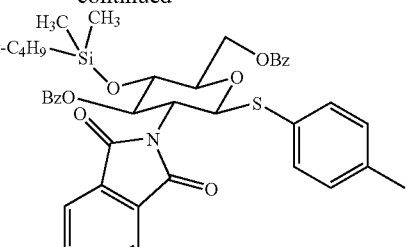

Monomer (I)

tBDMS = t-butyldimethylsilyl
Triflate = CF₃SO₃-

Product 6 (171.9 g; 275.6 mmol) was dissolved in minimum methylenechloride (350 mL) containing collidine (41.7 g; 344.5 mmol; 1.25 eq.). t-BDMS-Triflate (80.0 g; 303.1 mmol; 1.1 eq.) was added drop-wise by addition funnel (over 50 minutes). The reaction mixture was allowed to stir overnight. The reaction mixture was diluted with methylenechloride and washed sequentially with ice-cold water, 0.5 M aqueous HCL (ice cold), then aqueous saturated NaHCO₃. It was then dried with MgSO₄, filtered and concentrated to give monomer (I) as a white solid (207 g). The product was dissolved in dry toluene and concentrated to dryness before use in a glycosylation reaction. The 207 g of monomer (I) product recovered was essentially equal to the theoretical yield, calculated to be 203.4 g.

¹H-NMR (CD₂Cl₂) δ: 8.16-7.41 (benzoate hydrogens, phthalimido hydrogens), 7.30 & 6.95 (S-aromatic hydrogens), 5.97 (H-3), 5.82 (H-1), 4.89 & 4.49 (H-6), 4.40 (H-2), 4.14 (H-4), 4.01 (H-5), 2.30 (S-Ph-Me group), 0.80 (t-butyl group on silicon), 0.09&-0.16 (methyl groups of silicon). Thus the NMR spectrum verified the structure of Monomer (I), as shown above.

Example 3

Synthesis of Monomer (II)

Preparation of Intermediate Compound 7

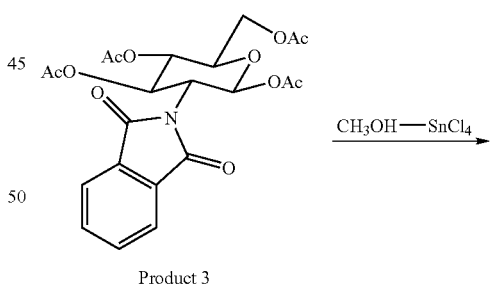

Product 3

CH₃OH—SnCl₄ →

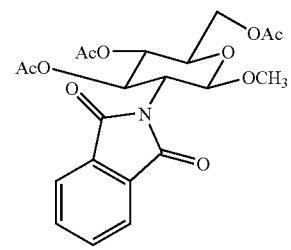

Product 7

To ensure that the starting glycoside was free of EtOH traces, compound 3 (60.0 g; 126 mmol) was dissolved in toluene and evaporated. It was then dissolved in anhydrous CH$_2$Cl$_2$ (500 ml) containing MeOH (6.5 g; 202 mmol; 1.6 eq.). Tin tetrachloride (SnCl$_4$; 18.4 g; 70.5 mmol; 0.56 eq.) was diluted with CH$_2$Cl$_2$ (25 ml) and added drop-wise. The reaction mixture was poured over ice water and shaken well. This was repeated once more and then the organic layer was washed twice with aqueous saturated NaHCO$_3$, dried with MgSO$_4$, filtered, and concentrated. The crude product was recrystallized from hot EtOH, giving crystals of product 7 (43.1 g). The crude yield of 49.8 g of product 7 was 88% of the theoretical yield, calculated to be 56.6 g, while the recrystallized product 7 yield of 43.1 g was 76%.

$^1$H-NMR (CD$_2$Cl$_2$) δ: 7.86-7.74 (phthalimido hydrogens), 5.78 (H-3), 5.31 (H-1), 5.18 (H-4), 4.31 (H-2), 4.34 & 4.20 (H-6), 3.88 (H-5), 2.20, 2.03, 1.86 (methyls of acetyl groups). Thus the NMR spectrum verified the structure of product 7, as shown above.

Preparation of Intermediate Product 8

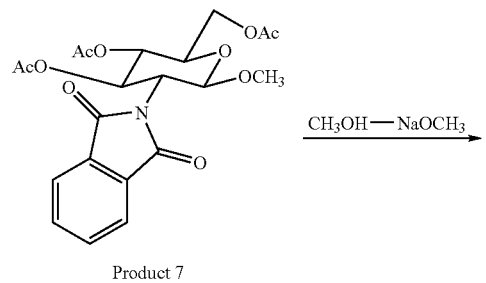

Product 7 (141.0 g; 314 mmol) was suspended in MeOH (1000 ml), and NaOMe (0.5 M, 10 ml) was added. The methyl glycoside product 7 did not readily dissolve in MeOH. The solution was tested to ensure basicity. The reaction was stirred overnight. The solution became clear. Examination of the reaction mixture by TLC (EtOAc-Hexane-EtOH=10:20:1) indicated the disappearance of the starting material and the formation of a polar product (near the origin). The solution was neutralized with sulfonic acid resin, filtered, and concentrated to dryness. Weight of the residue, called product 8, was 105.3 g, which probably includes some methanol.

The crude yield of 105.3 g of product 8 was essentially equal to the theoretical yield, calculated to be 101.3 g. $^1$H-NMR (CD$_3$OD) δ: 7.85-7.80 (phthalimido hydrogens), 5.07 (H-1), 4.21 (H-2), 3.94 (H-3), 3.92 & 3.74 (H-6), 3.40 (H-5), 3.40 (OCH$_3$), 3.38 (H-4). Thus the NMR spectrum verified the structure of product 8, as shown above.

Preparation of Monomer (II)

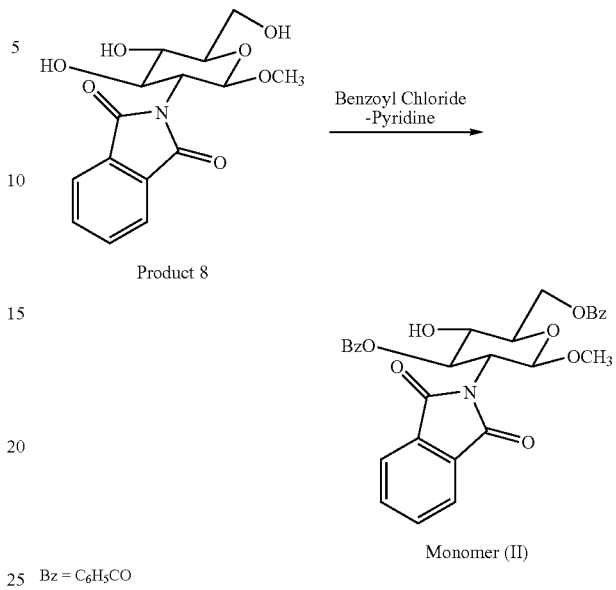

Bz = C$_6$H$_5$CO

Product 8 (crude; 105.3), after being evaporated with toluene-DMF, was suspended in CH$_2$Cl$_2$ (500 ml). Pyridine (61.8 g; 782 mmol; 2.5 eq.) was added first, followed by the drop-wise addition of benzoyl chloride (88 g; 626 mmol; 2.0 eq.) to the mixture. The reaction mixture was allowed to stir at room temperature for 24 h. It was then diluted with CH$_2$Cl$_2$ and washed sequentially with H$_2$O, 1 M HCl (2×), then aqueous saturated sodium bicarbonate solution, dried with MgSO$_4$, filtered, and concentrated. The product was purified by chromatography on silica gel, using EtOAc-Hexane=3:8 as eluant. The weight of the purified product was 116.1 g. The product was about 90% pure as determined by NMR. A portion (21.1 g) of this product was crystallized from diethylether-hexane to obtain pure crystalline material (13.8 g) of monomer (II).

$^1$H-NMR (CD$_2$Cl$_2$) δ: 8.15, 7.92, 7.67, 7.56, 7.42 (benzoate hydrogens), 7.83-7.74 (phthalimido hydrogens), 5.93 (H-3), 5.40 (H-1), 4.82 & 4.72 (H-6), 4.43 (H-2), 4.03-3.92 (H-5, H-4), 3.50 (OCH$_3$), 3.33 (OH). Thus the NMR spectrum verified the structure of monomer (II), as shown above.

Example 4

Synthesis of Derivatized Glucosamine Disaccharide

Structural Characterization of Oligoglucosamine Derivatives:

The structures of the coupled products described below were confirmed by proton NMR and mass spectrometry as follows. The chemical shifts of hydrogens H-3 and H-1 of the phthalimido glucosamine unit appeared in proton NMR spectrum at chemical shifts between 5 and 6.5 ppm. The hydrogen H-3 appeared as a doublet of a doublet with a coupling constant of about 8-10 Hz. By counting the number of these hydrogen signals, the length of the oligoglucosamine can easily be determined, for the disaccharide to the pentasaccharide. For oligoglucosamine derivatives of 6 and above, signals for these hydrogens started to overlap. However, a sufficient number of these signals could be identified to confirm the structure. A similar observation was seen for the anomeric hydrogens, which appeared as a doublet with a coupling constant of about 8-8.5 Hz, thereby confirming the β-glycosidic configuration. Furthermore, the chemical shift of H-4 in the terminal glucosamine unit appeared around 3.5 ppm, when the corresponding carbon carried a hydroxyl group. This was shifted to 3.7 ppm upon glycosylation at this site. Thus, H-4 could be used as a reporter group for establishing the success of the glycosylation reaction. Further proof of structure was obtained by MALDI and electrospray mass spectral data of the product, which are indicated for each compound.

Synthesis of Dimer Product 9

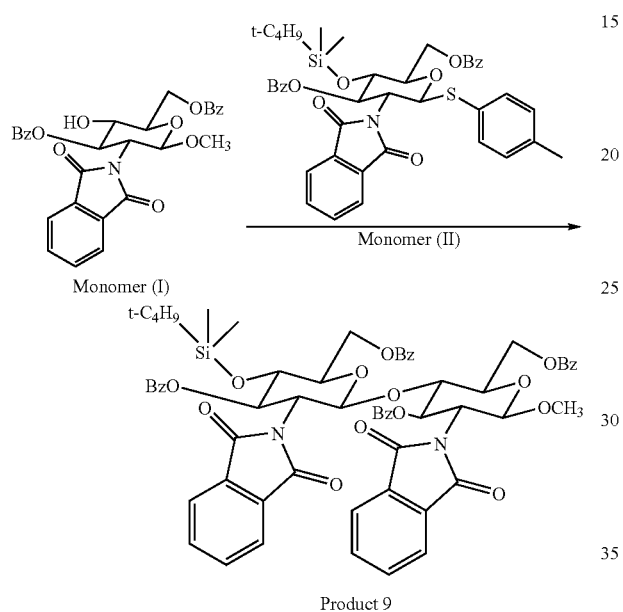

Product 9

Monomer (II) (80.6 g, 109.3 mmol, 1.2 eq.) and monomer (II) (48.4 g, 91.1 mmol), both previously evaporated with toluene once, were dissolved in $CH_2Cl_2$ (150 mL) in a 3-necked, 500 ml flask. 4A Molecular sieve was added (5 g). The mixture was cooled to −60° C. under nitrogen atmosphere with vigorous stirring. After 10 min, N-Iodosuccinimide (NIS; 44.3 g; 196.7 mmol; 2.2 eq.) was added as a dry powder, followed by the drop-wise addition of a solution of triflic acid (TfOH; 13.7 g, 91.1 mmol, 1.0 eq.) and methyltriflate (14.9 g, 54.8 mmol, 1.0 eq.) in methylenechloride. The reaction mixture was left at −55° C. for an additional 4 hr. An additional 100 ml of the triflic acid/methyltriflate solution was added to the reaction mixture dropwise to reduce of the viscosity. The reaction mixture was filtered cold over a celite pad into a filter flask containing 1:1 saturated sodium thiosulfate-sodium bicarbonate solution that was stirred thoroughly during the filtration. The flask and the residue on the filter were rinsed with methylenechloride and the combined filtrate was worked up as follows. The filtrate was poured into a separatory funnel. The contents were thoroughly mixed, the aqueous solution separated, and the organic layer washed one more time with saturated aqueous sodium thiosulfate solution, followed by water, and aqueous saturated sodium bicarbonate solution. The solution was then dried with magnesium sulfate, filtered and concentrated. Weight of the crude product was 111.1 g. Analytically pure sample was prepared by subjecting the crude product to separation by silica gel chromatography, using ethyl acetate-hexane as eluant. 1H-NMR ($CD_2Cl_2$) δ: 8.17-7.19 (phthalimido and benzoate hydrogens), 6.11 and 5.76 (2×H-3), 5.74 and 5.31 (2×H-1), 4.36 and 4.32 (2×H-2), 4.32 and 3.93 (2×H-4), 3.90 and 3.53 (2×H-5), 4.65, 4.38, 4.12, and 3.63 (4×H-6), 3.38 ($OCH_3$), 0.68 (t-butyl), −0.12, −0.40 (2×$CH_3$). Mass spec.: M. wt. Calc. 1144.37; Obs. M+Na=1167.5. Thus the NMR spectrum verified the structure of product 9, as shown above. The crude product as such was used in the next step, where complete removal of the tBDMS was accomplished.

Example 5

Removal of the Silicon Group from Disaccharide Product 9 for Chain Extension

Preparation of Intermediate Product 10

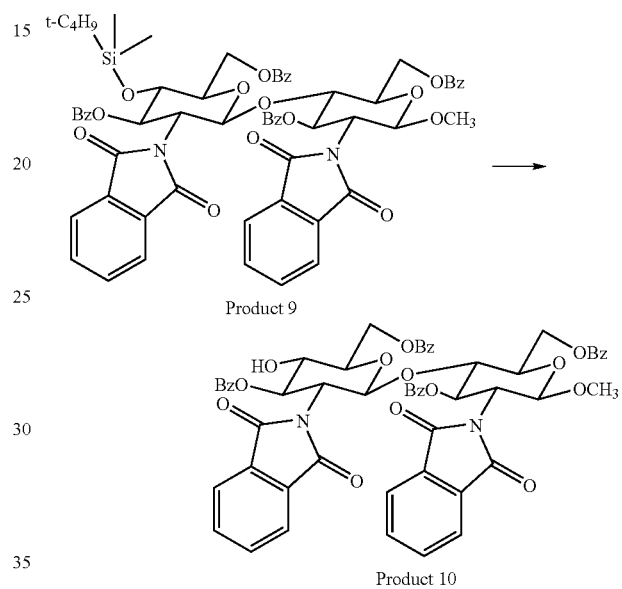

Product 9

Product 10

Product 9 (111.1 g) was dissolved in THF (350 ml). To this solution, a 1 M solution of acetic acid (110 ml) and a 1 M solution of n-tetrabutylammonium fluoride in THF (110 ml) were added and the reaction mixture was stirred at room temperature for 3 days. Completion of the reaction was ascertained by TLC using EtOAC:Hex:EtOH=4:8:1 as a solvent, which indicated that the reaction was complete. The solvent of the reaction was evaporated on high vacuum (without heat) and the residue was dissolved in $CH_2Cl_2$, washed sequentially with water, 1M aqueous HCl, 10% sodium thiosulfate aqueous solution, and finally, with saturated aqueous $NaHCO_3$. The solution was then dried with $MgSO_4$, filtered and concentrated. The resulting solid was treated with diethylether which resulted in a gluey material. The supernatent was filtered and the gluey material was repeatedly washed with diethylether. To the filtrate, hexane was added to precipitate any ether soluble product and this was filtered (Fraction B, 5.9 g). The final filtrate from ether-hexane was concentrated to dryness (Fraction C).

The NMR spectrum indicated that Fraction B product had about 5% silicon impurity (peak around 0 ppm) along with the major desired disaccharide. Fraction A was contaminated about 10% with tBDMS impurities and a tetrabutylammonium derivative. Therefore, Fraction A was resuspended in 600 ml of ether, mixed for about 10 minutes, filtered and the process was repeated once more (weight of the solid recovered was 77.3 g). This solid was purified once more by dissolving the product in ethyl acetate and precipitating the product with the aid of hexane (weight of the product recovered was 71.7 g). The filtrates were combined, hexane was added to precipitate the remaining product and additional 10.8 g of the product was recovered. $^1$H-NMR ($CD_2Cl_2$) δ: 8.12-7.14 (phthalimido and benzoate hydrogens), 6.14 and 5.73 (2×H-3), 5.72 and 5.34 (2×H-1), 4.37 and 4.34 (2×H-2), 4.10 and 3.69 (2×H-4), 3.97 and 3.44 (2×H-5), 4.66, 4.18, 4.12-4.06 (4×H-6), 3.38 (OCH$_3$), 3.35 (OH). Mass spec.: M. wt. Calc. 1030.98; Obs. M+Na=1053.1. Thus the NMR spectrum verified the structure of product 10, as shown above.

Example 6

Synthesis of Derivatized Glucosamine Trisaccharide

Synthesis of Trimer Product 11

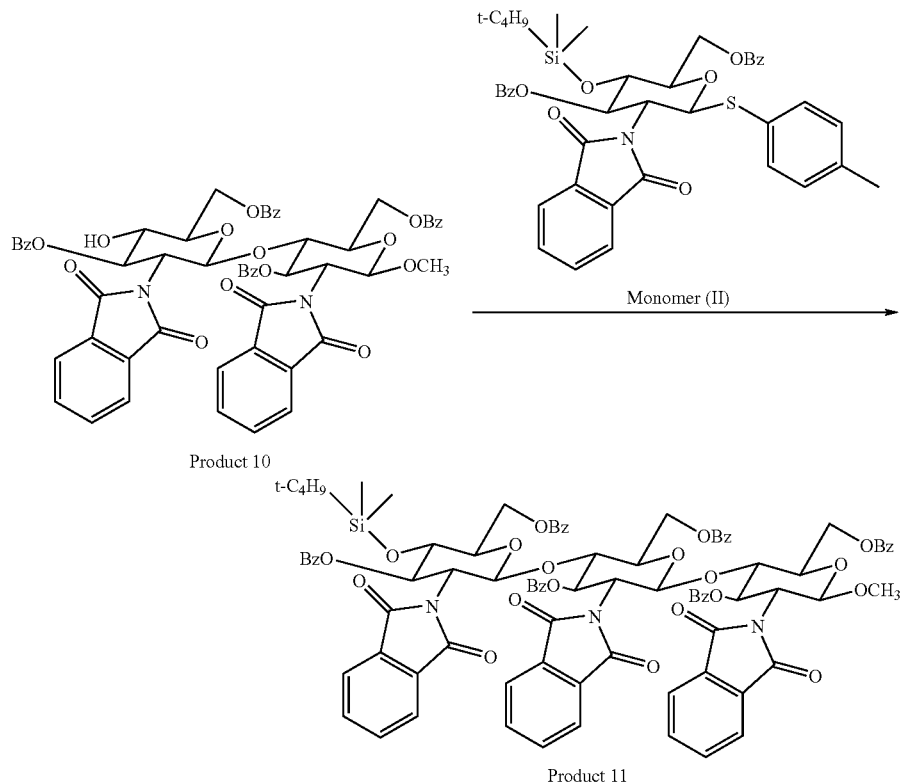

Product 10

Product 11

Monomer (I) (88.6 g; 120 mmol; 1.5 eq.) and product 10 (82.5 G; 80.0 mmol) were dissolved in CH$_2$Cl$_2$ (100 ml) in a flask. Molecular sieve (4A, 5.0 g) was added. The flask was placed in a −55° C. water bath and stirred for 15 min. NIS (48.6 g; 216 mmol) was added as a powder to the cold solution, while maintaining vigorous stirring. A solution of methyl triflate (13.1 g; 80 mmol; 1.0 eq.) and TfOH (12 g; 80 mmol; 1.9 eq.), both dissolved together in CH$_2$Cl$_2$ (5 ml), was added to the cold solution in drops by means of an addition funnel (over 60 min). After 6 h at −60° C. to −50° C., the reaction mixture was poured over saturated sodium bicarbonate and saturated sodium thiosulfate aqueous solution (1:1, 400 ml) contained in an Erlenmeyer flask and thoroughly stirred. Additional methylenechloride (200 ml) was added and the contents were thoroughly mixed for 10 min, the aqueous solution separated, and the organic layer washed with 0.6% aqueous bleach solution, de-ionized water, and aqueous saturated sodium bicarbonate solution. The solution was then dried with MgSO$_4$, filtered and concentrated.

To remove the excess monomer impurity from the trisaccharide, the crude product was suspended in diethylether (600 ml), the solid thoroughly mixed and the supernatent filtered. This process was repeated three times and the residue finally dissolved in methylenechloride, then concentrated to dryness giving 93.5 g of product 11. To the filtrate, about 40% volume of hexane was added and the precipitated material filtered, redissolved in methylenechloride and concentrated to dryness under vacuum to obtain an additional amount of compound 11 (26.0 g). $^1$H-NMR (CD$_2$Cl$_2$) δ (only select hydrogen chemical shifts are reported): 8.13-7.12 (phthalimido and benzoate hydrogens), 6.03, 5.88, and 5.62 (3×H-3), 5.64, 5.48, and 5.29 (3×H-1), 3.77 (H-4 of the terminal glucosamine unit), 3.90 (H-5 of the terminal glucosamine unit), 4.63 (H-6 of the terminal glucosamine unit), 3.35 (OCH$_3$), 0.64 (t-butyl), −0.18, −0.33 (2×CH$_3$ of the silicon unit). Mass spec.: Exact m. wt. Calc. 1643.49; Obs. M+Na=1666.3. Thus the NMR spectrum verified the structure of product 11, as shown above.

Example 7

Removal of the Silicon Group from Trisaccharide Product 11 for Further Chain Extension Preparation of Intermediate 12

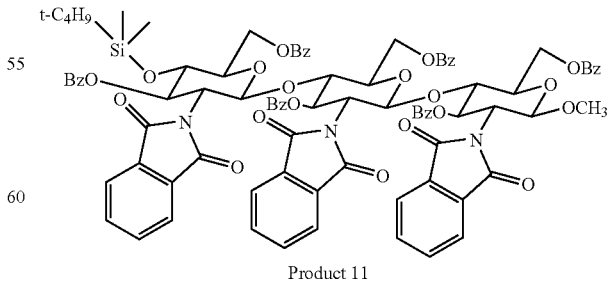

Product 11

↓

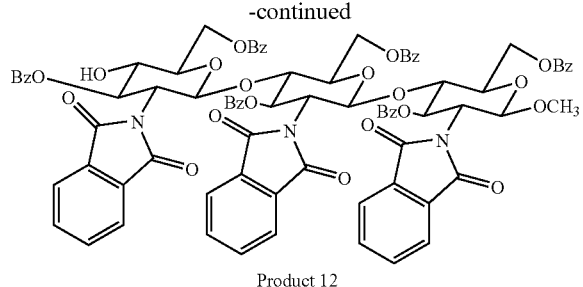

Product 12

Product 11 was dissolved in minimum THF (500 ml). To this solution, 1 M solution of acetic acid (150 ml) and a 1 M solution of n-tetrabutylammonium fluoride in THF (150 ml) were added and the reaction mixture was stirred at room temperature for 3 days. The reaction mixture was evaporated to dryness, the residue redissolved in methylenechloride, washed sequentially with deionized water, 1M HCl, 1% aqueous bleach solution (to remove the dark brown color), and saturated sodium bicarbonate solution, then concentrated to dryness.

In order to remove the nonpolar silicon and other impurities, the solid was dissolved in minimum ethyl acetate. Hexane was added in drops (the final solvent ratio EtOAc-Hexane was 17:14). This resulted in a gluey material. The liquid was filtered and the gluey material redissolved in EtOAc (200 ml) and precipitated with hexane (100 ml) as described above. Finally, diethylether was added to solidify the gluey material and the solid was filtered. The solid was redissolved in methylenechloride and concentrated to dryness giving 81.4 g of product 12.

The filtrate EtOAc-Hexane-ether was concentrated to dryness. The residue was suspended in diethylether, shaken well and filtered. This process was repeated twice. Finally, the precipitate was dissolved in methylenechloride and concentrated to dryness to obtain additional product 12 (16.5 g).). $^1$H-NMR (CD$_2$Cl$_2$) δ (only select hydrogen chemical shifts are reported): 8.08-7.16 (phthalimido and benzoate hydrogens), 6.03, 5.92, and 5.59 (3×H-3), 5.67, 5.48, and 5.29 (3×H-1), 3.56 (H-4 of the terminal glucosamine unit), 3.91 (H-5 of the terminal glucosamine unit), 4.63 (H-6 of the terminal glucosamine unit), 3.35 (OCH$_3$), 3.01 (OH), 0.64. Mass spec: Exact m. wt. Calc. 1529.41; Obs. M+Na=1553.4. Thus the NMR spectrum verified the structure of product 12, as shown above.

Example 8

Synthesis of Derivatized Glucosamine Tetrasaccharide

Synthesis of the Tetramer Product 13

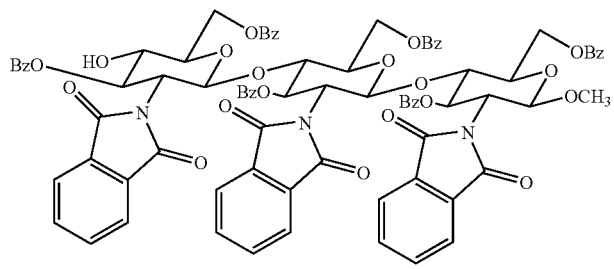

Product 12

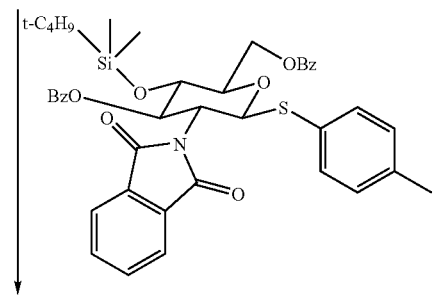

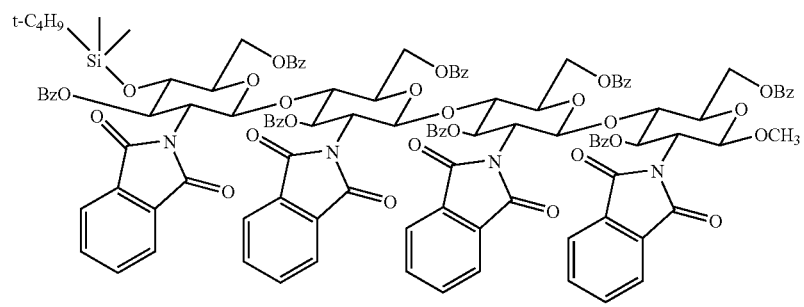

Product 13

Thioglycoside monomer (I) (37.4 g; 50.7 mmol) and trisaccharide product 12 (45.6 g; 29.8 mmol) were dissolved in CH$_2$Cl$_2$ (150 ml) in a flask. Molecular sieve (4A, 10.0 g) was added. The flask was placed in a −55° C. bath and stirred for 15 min. NIS (20.5 g; 91.25 mmol) was added as a powder to the cold solution, while maintaining vigorous stirring. A solution of methyl triflate (4.9 g; 29.8 mmol) and TfOH (4.5 g; 29.8 mmol), both dissolved together in CH$_2$Cl$_2$ (20 ml), was added to the cold solution in drops by means of an addition funnel (over 60 min). After 6 h, at −60° C., the reaction mixture was poured over saturated sodium bicarbonate and saturated sodium thiosulfate aqueous solution (1:1, 400 mL) contained in an Erlenmeyer flask and thoroughly stirred. Additional methylenechloride (200 ml) was added and the contents were thoroughly mixed for 10 min, the aqueous solution separated, and the organic layer washed sequentially with 10% aqueous sodium thiosulfate solution, 1% aqueous bleach solution, and aqueous saturated sodium bicarbonate solution. The solution was then dried with MgSO$_4$, filtered and concentrated (75.1 g).

To remove the excess monomer impurity from the tetrasaccharide, the crude product was suspended in diethylether (600 ml), the solid thoroughly mixed and the supernatent filtered. This process was repeated three times, and the residue finally dissolved in methylenechloride and concentrated to dryness (13 A, 54.2 g).

To the filtrate, about 40% volume of hexane was added and the precipitated material filtered, redissolved in methylenechloride and concentrated to dryness giving 5.8 g of product 13 B. NMR analysis of 13 A and 13 B indicated that these were nearly the same and they were combined. $^1$H-NMR (CD$_2$Cl$_2$) δ (only select hydrogen chemical shifts are reported): 8.09-7.03 (phthalimido and benzoate hydrogens), 6.00, 5.83, 5.76, and 5.62 (4×H-3), 5.62, 5.42, 5.41, and 5.27 (4×H-1), 3.74 (H-4 of the terminal glucosamine unit), 3.88 (H-5 of the terminal glucosamine unit), 4.60 (H-6 of the terminal glucosamine unit), 3.33 (OCH$_3$), 0.63 (t-butyl), −0.19, −0.34 (2×CH$_3$ of the silicon unit). Mass spec.: Exact m. wt. Calc. 2142.62; Obs. M+Na=2166.4. Thus the NMR spectrum verified the structure of product 13, as shown above.

Example 9

Coversion of Benzoyl and Phthalimido Protecting Groups to Their Acetates

Synthesis of Acetylated Product 15 from 13

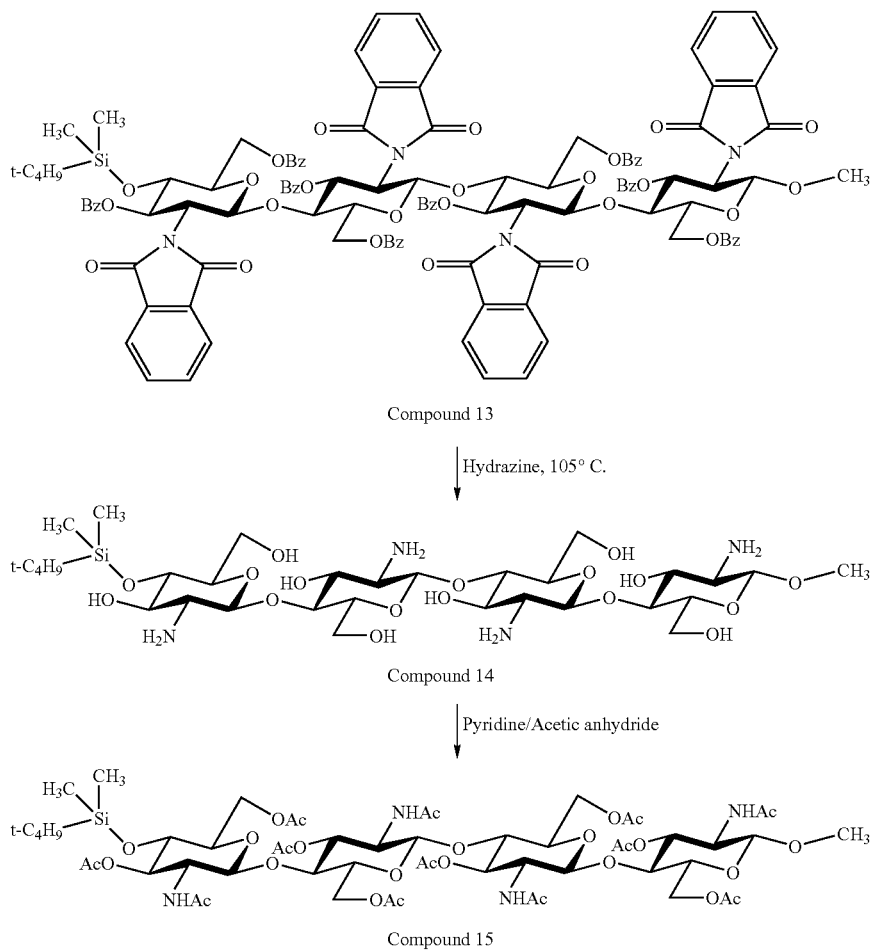

Product 13 is dissolved in hydrazine and heated to 105° C. After 20 h, the reaction mixture is concentrated to dryness. The residue is then extensively washed with methylenechloride to remove the by-products and to give product 14.

Product 14 is dissolved in minimum amount of anhydrous pyridine containing equal volume of acetic anhydride. A small amount of 4-N,N-dimethylamino pyridine is added and the reaction is stirred at room temperature for 24 h. It is then poured over ice-water and is extracted with methylenechloride. The methylenechloride layer is washed with ice-cold 1M aqueous hydrochloric acid, and then saturated sodium bicarbonate solution. It is then dried over anhydrous magnesium sulfate and concentrated under reduced pressure to obtain product 15.

Example 10

Desilylation and Addition of Terminal Phthalimido-Glucosamine Unit

Synthesis of De-Silylated Product 16

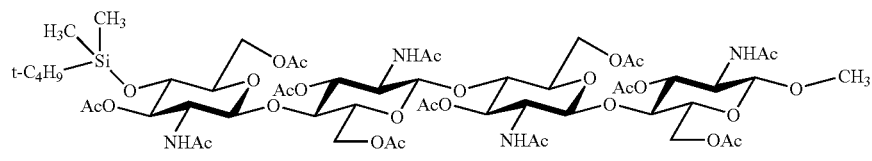

Compound 15

↓ nBu₄NF-CH₃COOH/THF

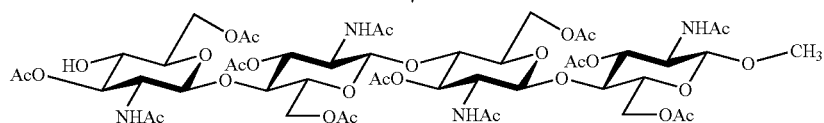

Compound 16

Tetrasaccharide 15 is dissolved in minimum THF followed by the addition of 1 M solution of acetic acid in THF and 1 M solution of tetrabutylammoniumfluoride in THF and stirred at room temperature. Reaction progress is checked after 18 h by NMR for completion of the reaction. The reaction mixture is evaporated to dryness, redissolved in methylenechloride, washed sequentially with saturated sodium thiosulfate solution, 1M HCl, and saturated sodium bicarbonate solution, then concentrated to dryness.

To remove nonpolar silicon impurities, the solid is dissolved in ethyl acetate (400 ml). Hexane (400 ml) is added in drops with stirring of the precipitated material. The precipitate is filtered and the process is repeated once more, followed by a final washing of the solid with 1:1 EtOAc-Hexane and then is dried to get product 16.

Glycosylation of Tetrasaccharide

Synthesis of Tetrasaccharide Product 17

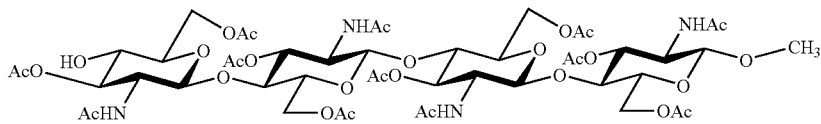

Compound 16

↓ TfOH
Methyl-triflate
NIS
Methylene chloride

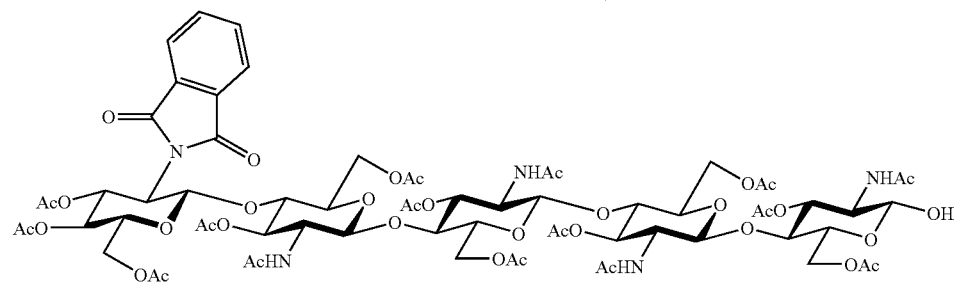

Compound 17

Thioglycoside monomer (Product 4 from Example 2; 2 mole equivalent to product 16) and tetrasaccharide product 16 are dissolved in minimum CH$_2$Cl$_2$ containing 4A Molecular sieves. The solution is cooled to −60° C. and is stirred well. After ten minutes at −60° C., NIS (3.5 mole equivalent to pentamer 16) is added quickly. After five minutes, a solution of triflic acid (1 equivalent) and methyl triflate (1 equivalent), dissolved together in CH$_2$Cl$_2$ (20 ml), is added in drops. The reaction mixture is left at −60° C. for an additional 5 hr. The reaction mixture is poured over saturated sodium bicarbonate and saturated sodium thiosulfate aqueous solution (1:1, 500 ml) contained in an Erlenmeyer flask and is thoroughly stirred. Additional methylenechloride is added and the contents are thoroughly mixed for 10 min, the aqueous solution is separated, and the organic layer is washed sequentially with 1% aqueous bleach solution, 10% aqueous sodium thiosulfate solution, and aqueous saturated sodium bicarbonate solution. The solution is then dried with MgSO$_4$, filtered and concentrated. The residual solid is dissolved in minimum EtOAc, and is followed by dropwise addition of hexane. The liquid portion is filtered, and the insoluble material is redissolved in EtOAc, then precipitated again in hexane. Finally, diethylether is added to solidify the gluey material, and the residue is washed with ether and dried to get product 17.

Example 11

Removal of O-Acetyl and N-Phthalimido Groups and Conversion to Lipochitooligosaccharide Synthesis of Product 18

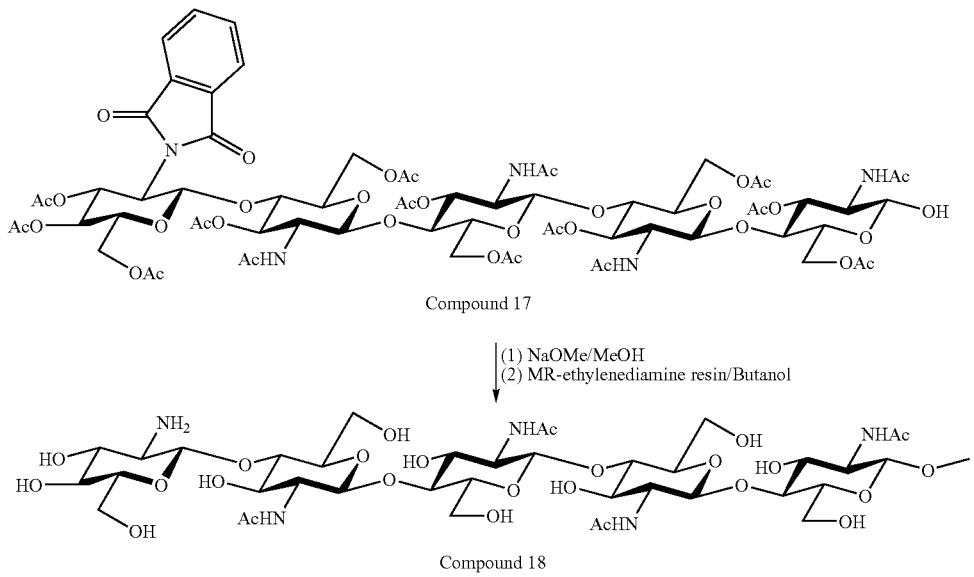

Compound 17

(1) NaOMe/MeOH
(2) MR-ethylenediamine resin/Butanol

Compound 18

Product 17 is suspended in MeOH, then NaOMe (0.5 M) is added and is stirred at room temperature for 2 days. The reaction is neutralized with acidic resin, and is concentrated to dryness. The product is then suspended in n-butanol containing MR-ethylenediamine resin and heated to 100° C. for 24 h. The hot solution is filtered over a celite pad and is washed with 1:1 methanol-water. The combined filtrate is concentrated to dryness to obtain product 18.

Synthesis of Lipochitooligosaccharide 19:

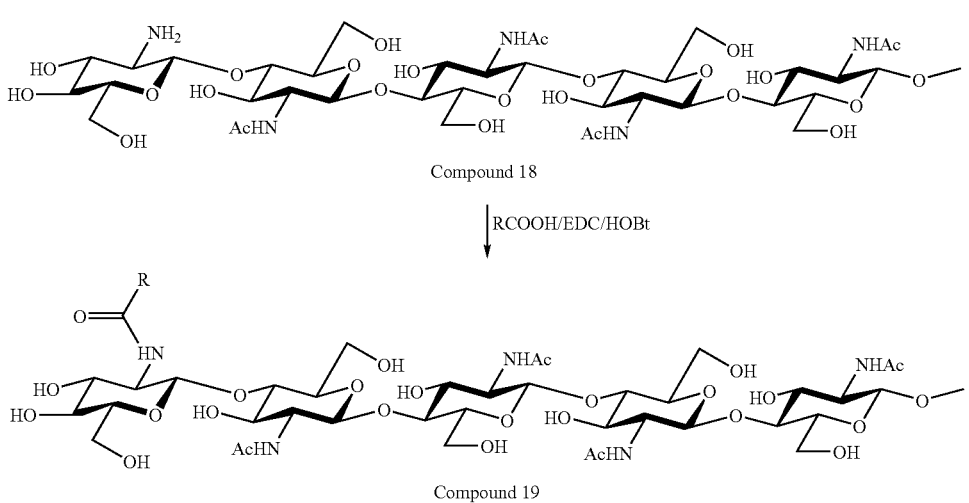

Compound 18

RCOOH/EDC/HOBt

Compound 19

Product 18 is dissolved in minimum water containing the 2E,9Z-hexadecadienoic acid for amidation of the amine group of the terminal glucosamine unit. Ethyl-(N,N-dimethylaminopropyl)-carbodiimide hydrochloride (1 equivalent) and N-hydroxybenzotriazole (1 equivalent) are added and stirred at room temperature overnight. The reaction mixture is passed through a column of acidic resin and the filtrate is concentrated to dryness to get product 19.

Example 12

Synthesis of a Lipochitooligosaccharide Tetramer

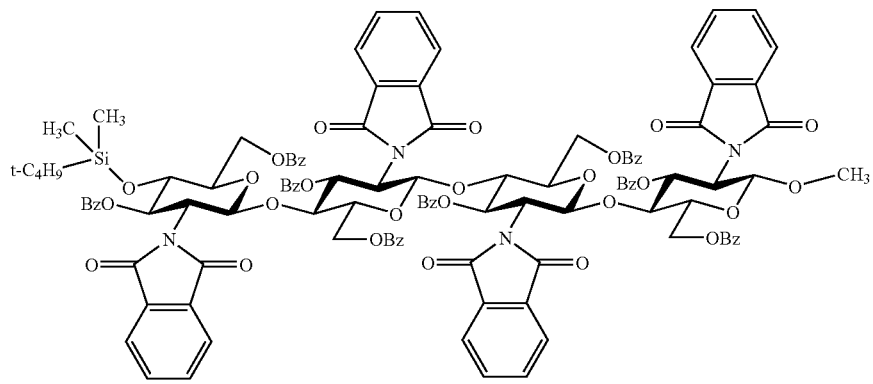

Product 13

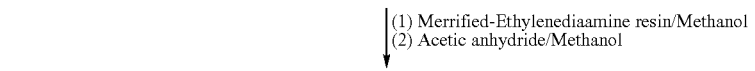

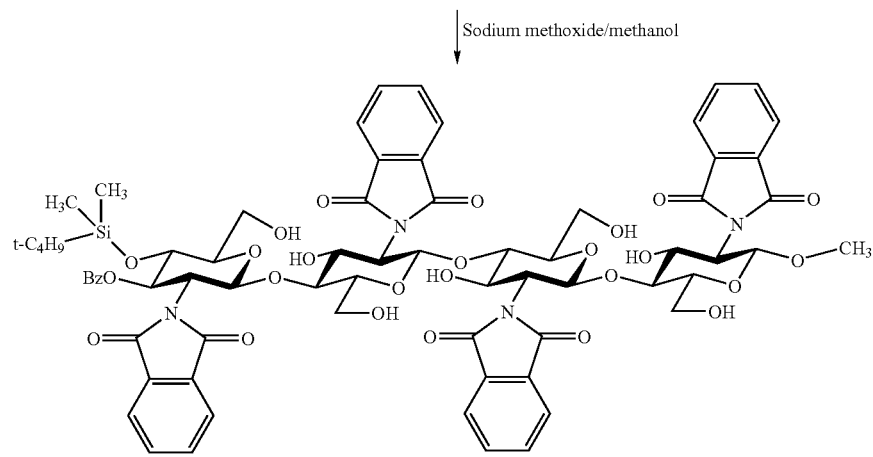

Product 20

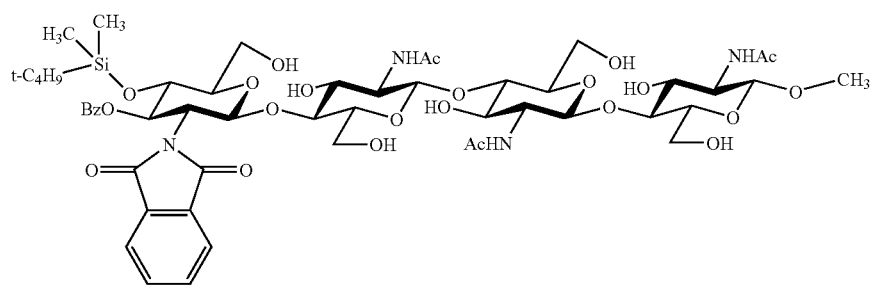

Product 21

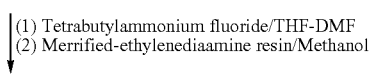

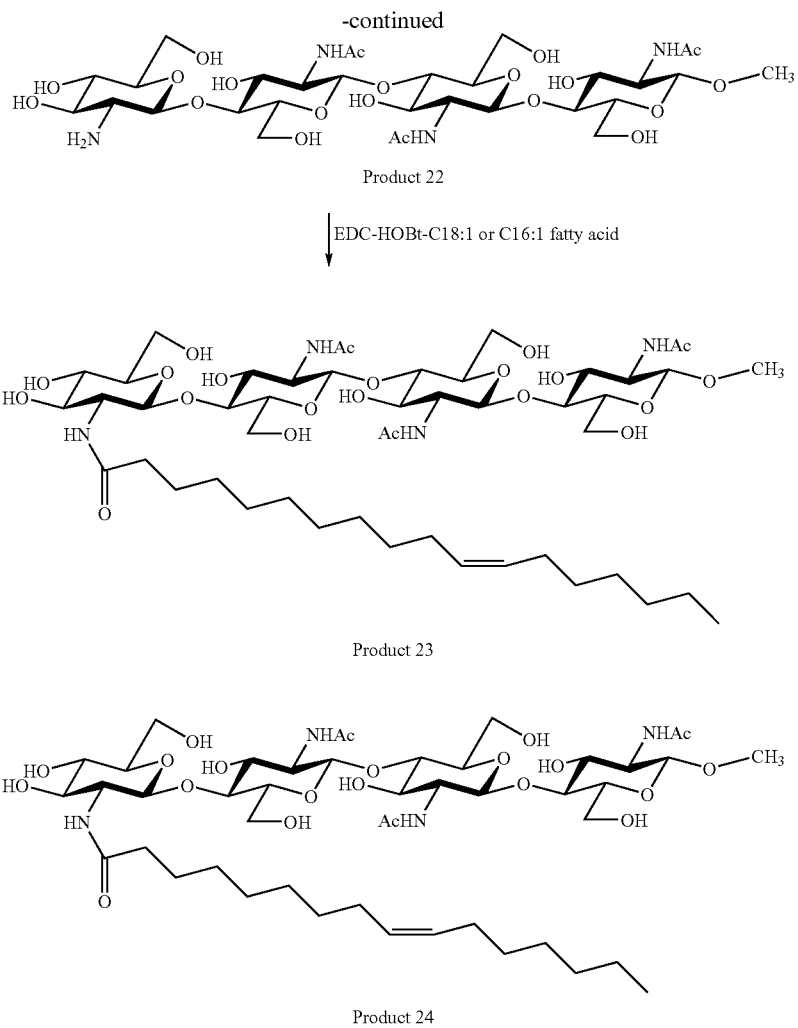

Product 22

Product 23

Product 24

Product tetrasaccharide 13 of Example 8 (25 g) was suspended in anhydrous methanol (900 ml). Sodium methoxide solution (0.5 M, 20 ml) was added and the reaction mixture was stirred at room temperature for 1 day, forming a thick white precipitate. The reaction mixture was then heated to reflux causing all of the solid to dissolve. After 72 h at reflux, lots of precipitate was again formed in the reaction flask. The heating was stopped, the flask was cooled, and the precipitated material was filtered and washed with methanol. Weight of the precipitated product was 11.2 g. This was identified as product 20 by proton NMR.

Product 20 (11.2 g) was refluxed in methanol (1 L) containing ethylenediamine Merrifield resin (152 g) for 5 days. The warm reaction mixture was then filtered and washed with methanol. Unreacted starting material remained as solid, whereas the methanolic filtrate contained product. This was concentrated to dryness and the solid was suspended in methanol (175 ml) containing acetic anhydride (6 ml) and triethylamine (6 ml), and stirred at room temperature for 2 h. A white precipitate formed in the flask, which was filtered. The filtrate was treated with H+ resin (10 g), filtered, and concentrated to dryness to get product 21 (6.7 g). This was identified as product 21 by proton NMR.

Product 21 was suspended in tetrahydrofuran (100 ml), and 1M solutions of acetic acid and tetrabutylammonium fluoride (5 ml each) were added. After 24 h of stirring at room temperature the mixture remained cloudy. N,N-dimethylformamide (10 ml) was added to assist in dissolving the product, and the reaction was stirred at 65° C. for 3 days and then concentrated to dryness. The resulting product was then suspended in methanol (100 ml) and ethylenediamine Merrifield resin (25 g) was added. The reaction was heated to 75° C. and stirred for 44 h. The reaction was allowed to cool to room temperature and filtered. The filtrate which contained product 22 was concentrated to dryness (2.2 g). This was identified as product 22 by proton NMR.

A solution of the fatty acid C18:1 or C16:1 (0.37 g) in N,N-dimethylformamide (10 ml) containing EDC (0.28 g) and HOBt-H$_2$O (0.20 g) was added to a suspension of product 16 (1.0 g) in DMF. Additional N,N-dimethylformamide (10 ml) was added to completely dissolve the oligomer. The reaction mixture was stirred for 18 h at room temperature and then heated to 80° C. for 2 h, resulting in the formation of a thick gel. The gel was diluted with methanol and the gelatinous material containing the product (product 23 from C18:1 and product 24 from C16:1) was filtered. The residue was repeatedly washed with methanol, followed by washing with water. The residue on the filter paper was collected and dried to obtain product 23 (520 mg) or product 24 (552 mg). This was identified as product 23 and 24 by proton NMR.

What is claimed is:

1. A process for synthesizing a lipochitooligosaccharide compound having the structure:

Structure A

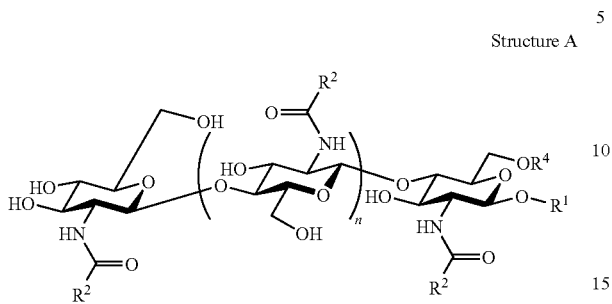

where individual groups $R^1$ and $R^2$ are independently selected from the group consisting of: H, $C_1$ to $C_{20}$ alkyl and aralkyl, aryl, $C_2$ to $C_{20}$ mono, di or polyalkenyl groups, and $C_2$ to $C_{20}$ mono, di or polyalkynyl groups; $R^3$ is selected from the group consisting of $C_1$ to $C_{20}$ alkyl and aralkyl, aryl, $C_2$ to $C_{20}$ mono, di or polyalkenyl groups, and $C_2$ to $C_{20}$ mono, di or polyalkynyl, groups; $R^4$ is selected from the group consisting of monosaccharides, sulfates and phosphates; and n is from 0 to about 20;

said process comprising:

a) providing a compound of structure D

Structure D

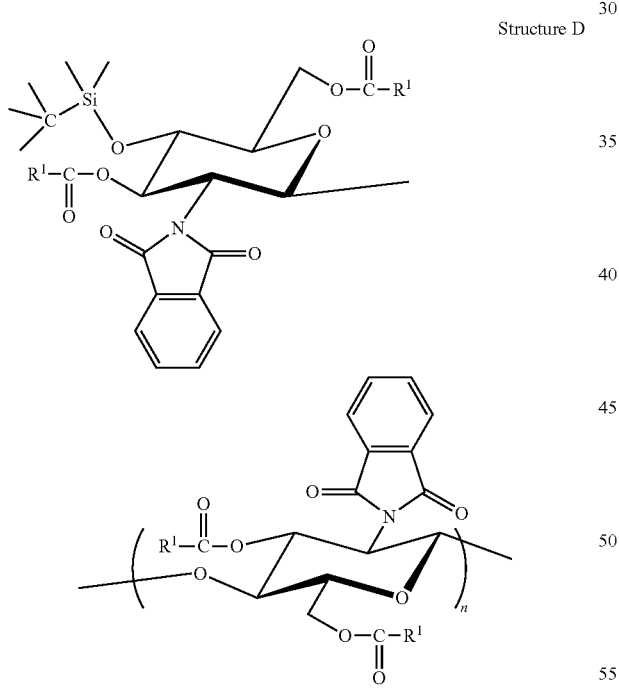

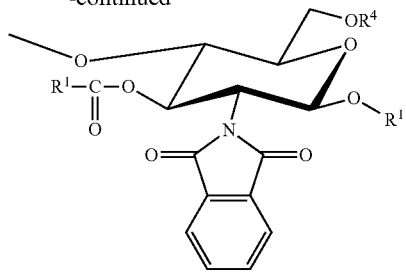

wherein $R^1$ is selected from the group consisting of H, $C_1$ to $C_{20}$ alkyl and aralkyl, aryl, $C_2$ to $C_{20}$ mono, di or polyalkenyl groups, and $C_2$ to $C_{20}$ mono, di or polyalkynyl groups;

b) removing the ester groups and the N-phthalimido groups of non-silylated sugar units of the compound of structure D by first removing the ester groups by transesterification and second removing N-phthalimido groups using an ethylenediamine Merrifield resin to form an amino-sugar product;

c) selectively reacting the amino groups on the non-silylated sugar units of the amino-sugar product of (b) with an acylating reagent to make an N-acyl derivative product;

d) removing the silyl group on the silylated sugar unit of the N-acyl derivative product of (c) by reacting the N-acyl derivative product with tetra-N-alkyl ammonium fluoride to make a de-silylated product;

e) removing the ester and the N-phthalimido group of the de-silylated product of (d) by reacting the de-silylated product with an ethylenediamine Merrifield resin under refluxing conditions to produce a de-N-phthalimidated product;

f) acylating the terminal amino group of the de-N-phthalimidated product of (e) with fatty acids activated with carbodiimide and N-hydroxybenzotriazole, or an acid halide of the formula $R^1COX$, in the presence of a base catalyst, where X is a halide, and $R^1$ is selected from the group consisting of H, $C_1$ to $C_{20}$ alkyl and aralkyl, aryl, $C_2$ to $C_{20}$ mono, di or polyalkenyl groups, and $C_2$ to $C_{20}$ mono, di or polyalkynyl groups; to form a lipochitooligosaccharide; and g) isolating the lipochitooligosaccharide.

2. The process of claim 1 wherein the acylating agent of (c) is acetic anhydride.

3. The process of claim 1 wherein the tetra-N-alkyl ammonium fluoride of (d) is tetra-n-butyl ammonium fluoride.

* * * * *